US011903557B2

United States Patent
Lord et al.

(10) Patent No.: US 11,903,557 B2
(45) Date of Patent: Feb. 20, 2024

(54) ENDOSCOPE FOR IMAGING IN NONVISIBLE LIGHT

(71) Applicant: Pristine Surgical LLC, Manchester, NH (US)

(72) Inventors: Bryan Lord, Bedford, NH (US); John M. Cronk, Strafford, NH (US)

(73) Assignee: PSIP2 LLC, Manchester, NH (US)

( * ) Notice: Subject to any disclaimer, the term of this patent is extended or adjusted under 35 U.S.C. 154(b) by 287 days.

(21) Appl. No.: 16/863,509

(22) Filed: Apr. 30, 2020

(65) Prior Publication Data

US 2020/0345218 A1    Nov. 5, 2020

Related U.S. Application Data

(60) Provisional application No. 62/841,163, filed on Apr. 30, 2019.

(51) Int. Cl.
*A61B 1/00* (2006.01)
*G06T 7/30* (2017.01)
(Continued)

(52) U.S. Cl.
CPC ...... *A61B 1/000095* (2022.02); *A61B 1/0005* (2013.01); *A61B 1/00078* (2013.01);
(Continued)

(58) Field of Classification Search
CPC ... A61B 1/0005; A61B 5/0035; A61B 5/7425; A61B 5/7267; A61B 1/000096;
(Continued)

(56) References Cited

U.S. PATENT DOCUMENTS

| 4,273,110 A | 6/1981 | Groux |
| 4,765,313 A | 8/1988 | Kumakura |

(Continued)

FOREIGN PATENT DOCUMENTS

| CN | 2551172 Y | 5/2003 |
| CN | 2868212 Y | 2/2007 |

(Continued)

OTHER PUBLICATIONS

PCT/IB2019/054783, ISA/210 International Search Report and ISA/237 Written Opinion of the International Searching Authority (dated Oct. 24, 2019).

(Continued)

*Primary Examiner* — Boubacar Abdou Tchoussou
(74) *Attorney, Agent, or Firm* — Potomac Law Group, PLLC; David E. Boundy

(57) ABSTRACT

An endoscope. One or more image sensors are designed to capture image data in visible light. One or more image sensors are designed to capture image data in a nonvisible portion of the electromagnetic spectrum. An insertion shaft is designed to support the visible and nonvisible image sensors at or near a distal tip with sufficient rigidity to permit guidance to a surgical site in a human body. Image processing software is trained through machine learning to enhance image quality of at least the nonvisible portion of the image, and to present the enhanced nonvisible image as a real-time, visible presentation to a surgeon. A handle has electronics for drive of illumination circuitry and to receive imaging signal from the imaging circuitry. A joint between the proximal handle portion and the insertion shaft is designed to separably connect the insertion shaft to the proximal handle portion. When separated, the joint permits removal of the insertion shaft for disposal and replacement.

20 Claims, 24 Drawing Sheets

(51) Int. Cl.

| | |
|---|---|
| *A61B 5/00* | (2006.01) |
| *A61B 1/06* | (2006.01) |
| *A61B 1/05* | (2006.01) |
| *A61B 1/04* | (2006.01) |
| *G06T 5/00* | (2006.01) |
| *H04N 5/262* | (2006.01) |
| *H04N 5/272* | (2006.01) |
| *H04N 5/265* | (2006.01) |
| *H04N 23/45* | (2023.01) |
| *H04N 23/54* | (2023.01) |
| *H04N 23/74* | (2023.01) |
| *H04N 23/50* | (2023.01) |
| *A61M 31/00* | (2006.01) |

(52) U.S. Cl.
CPC .... *A61B 1/000096* (2022.02); *A61B 1/00103* (2013.01); *A61B 1/00105* (2013.01); *A61B 1/043* (2013.01); *A61B 1/05* (2013.01); *A61B 1/0684* (2013.01); *A61B 5/0035* (2013.01); *A61B 5/0071* (2013.01); *A61B 5/0086* (2013.01); *A61B 5/7267* (2013.01); *A61B 5/7425* (2013.01); *A61M 31/005* (2013.01); *G06T 5/00* (2013.01); *G06T 7/30* (2017.01); *H04N 5/265* (2013.01); *H04N 5/2624* (2013.01); *H04N 5/272* (2013.01); *H04N 23/45* (2023.01); *H04N 23/54* (2023.01); *H04N 23/74* (2023.01); *G06T 2207/10048* (2013.01); *G06T 2207/10068* (2013.01); *G06T 2207/10152* (2013.01); *G06T 2207/20081* (2013.01); *G06T 2207/20221* (2013.01); *H04N 23/555* (2023.01)

(58) Field of Classification Search
CPC .. A61B 1/000095; H04N 5/2624; H04N 5/33; G06T 2207/20221; G06T 5/00; G06T 2207/20081
See application file for complete search history.

(56) References Cited

U.S. PATENT DOCUMENTS

| | | |
|---|---|---|
| 4,852,551 A | 8/1989 | Opie |
| 4,895,138 A | 1/1990 | Yabe |
| 4,919,112 A | 8/1990 | Siegmund |
| 4,964,710 A | 10/1990 | Leiner |
| 4,997,084 A | 3/1991 | Opie |
| 5,165,387 A | 11/1992 | Woodson |
| 5,188,092 A | 2/1993 | White |
| 5,377,047 A | 12/1994 | Broome |
| 5,519,532 A | 5/1996 | Broome |
| 5,573,493 A | 11/1996 | Sauer |
| 5,653,677 A | 8/1997 | Okada |
| 5,711,755 A | 1/1998 | Bonnell |
| 5,718,664 A | 2/1998 | Peck |
| 5,892,630 A | 4/1999 | Broome |
| 6,293,910 B1 | 9/2001 | Yamakita |
| 6,605,260 B1 | 8/2003 | Busted |
| 6,652,452 B1 | 11/2003 | Seifert |
| 6,865,825 B2 | 3/2005 | Bailey |
| 7,033,317 B2 | 4/2006 | Pruitt |
| 7,239,805 B2 | 7/2007 | Uyttendaele |
| 7,413,543 B2 | 8/2008 | Banik |
| 7,427,262 B2 | 9/2008 | Bonningue |
| 7,479,106 B2 | 1/2009 | Banik |
| 7,530,946 B2 | 5/2009 | Hartwick |
| 7,976,559 B2 | 7/2011 | Goldfarb |
| 8,187,170 B2 | 5/2012 | Naito |
| 8,257,386 B2 | 9/2012 | Lee |
| 8,398,540 B2 | 3/2013 | Hassidov |
| 8,449,456 B2 | 5/2013 | Ueno |
| 8,556,806 B2 | 10/2013 | Farr |
| 8,827,899 B2 | 9/2014 | Farr |
| 8,858,425 B2 | 10/2014 | Farr |
| 9,066,658 B2 * | 6/2015 | Hamel .................. G16Z 99/00 |
| 9,107,574 B2 | 8/2015 | Goldfarb |
| 9,116,282 B2 | 8/2015 | Kazakevich |
| 9,242,069 B2 | 1/2016 | Alt |
| 9,271,637 B2 | 3/2016 | Farr |
| 9,364,249 B2 | 6/2016 | Kimball |
| 9,504,373 B2 | 11/2016 | Vayser |
| 9,877,654 B2 | 1/2018 | Tesar |
| 9,895,048 B2 | 2/2018 | Ouyang |
| 10,105,040 B2 | 10/2018 | Ochi |
| 10,278,563 B2 | 5/2019 | Ouyang |
| 10,780,187 B2 | 9/2020 | Kang |
| 11,141,045 B2 | 10/2021 | Kucharski |
| 11,185,216 B2 | 11/2021 | Heni |
| 11,278,194 B2 | 3/2022 | Benning |
| 11,357,593 B2 * | 6/2022 | Komp ................ A61B 1/00193 |
| 2001/0031115 A1 | 10/2001 | Chen |
| 2004/0098040 A1 | 5/2004 | Taniguchi |
| 2006/0149127 A1 | 7/2006 | Seddiqui |
| 2006/0276692 A1 | 12/2006 | Kucklick |
| 2007/0202005 A1 | 8/2007 | Maschke |
| 2007/0225556 A1 | 9/2007 | Ortiz |
| 2007/0249904 A1 | 10/2007 | Amano |
| 2008/0027283 A1 | 1/2008 | Matsui |
| 2008/0051802 A1 | 2/2008 | Schostek |
| 2008/0300456 A1 | 12/2008 | Irion |
| 2009/0076329 A1 | 3/2009 | Su |
| 2009/0082630 A1 | 3/2009 | Tulley |
| 2010/0198009 A1 | 8/2010 | Farr |
| 2010/0204546 A1 | 8/2010 | Hassidov |
| 2011/0009694 A1 | 1/2011 | Schultz |
| 2011/0028790 A1 | 2/2011 | Farr |
| 2011/0237880 A1 * | 9/2011 | Hamel ............. A61B 1/000094 |
| | | 600/104 |
| 2012/0029280 A1 | 2/2012 | Kucklick |
| 2012/0116398 A1 | 5/2012 | Goldfarb |
| 2013/0012783 A1 | 1/2013 | Vayser |
| 2013/0253499 A1 | 9/2013 | Kimball |
| 2014/0107416 A1 | 4/2014 | Birnkrant |
| 2014/0114129 A1 | 4/2014 | Peh |
| 2014/0221749 A1 | 8/2014 | Grant |
| 2014/0275771 A1 | 9/2014 | Henley |
| 2015/0011830 A1 | 1/2015 | Hunter |
| 2015/0025311 A1 | 1/2015 | Kadan |
| 2015/0069728 A1 | 3/2015 | Seitz, III |
| 2015/0164313 A1 | 6/2015 | Ouyang |
| 2015/0173594 A1 | 6/2015 | Farhadi |
| 2015/0327886 A1 | 11/2015 | Shen |
| 2015/0374210 A1 | 12/2015 | Durr |
| 2016/0235286 A1 | 8/2016 | Chiang |
| 2017/0070654 A1 | 3/2017 | Ochi |
| 2017/0078583 A1 | 3/2017 | Haggerty |
| 2017/0182194 A1 | 6/2017 | Shin |
| 2017/0188795 A1 | 7/2017 | Ouyang |
| 2017/0245890 A1 | 8/2017 | Ochi |
| 2018/0084986 A1 | 3/2018 | Ochi |
| 2018/0168442 A1 | 6/2018 | Schaeffer |
| 2018/0235441 A1 | 8/2018 | Huang |
| 2019/0038116 A1 | 2/2019 | Ochi |
| 2019/0298151 A1 * | 10/2019 | Frangioni .............. H04N 5/332 |
| 2019/0328217 A1 | 10/2019 | Moreau |
| 2019/0374095 A1 | 12/2019 | Lord |
| 2020/0000491 A1 | 1/2020 | Washburn |
| 2020/0222146 A1 * | 7/2020 | Komp .................. A61B 90/361 |
| 2020/0397232 A1 | 12/2020 | Ulmschneider |
| 2021/0052145 A1 | 2/2021 | Rauniyar |
| 2021/0169316 A1 | 6/2021 | Schultheis |
| 2021/0220014 A1 | 7/2021 | Gitelis |
| 2021/0330177 A1 * | 10/2021 | Koh .................. A61B 1/00174 |
| 2022/0125280 A1 * | 4/2022 | Tyan .................. A61B 5/0035 |
| 2022/0378279 A1 | 12/2022 | Poll |

(56) References Cited

U.S. PATENT DOCUMENTS

| | | |
|---|---|---|
| 2023/0070386 A1 | 3/2023 | Koubi |
| 2023/0123867 A1 | 4/2023 | Herda |

FOREIGN PATENT DOCUMENTS

| | | |
|---|---|---|
| CN | 101040775 | 9/2007 |
| CN | 101801278 | 8/2010 |
| CN | 103315807 | 9/2013 |
| CN | 106308727 | 1/2017 |
| CN | 106821285 | 6/2017 |
| CN | 107157429 | 9/2017 |
| CN | 111458859 | 7/2020 |
| DE | 10330177 A1 | 3/2005 |
| EP | 1634656 | 3/2006 |
| EP | 2266452 | 12/2010 |
| JP | 2001-128923 A | 5/2001 |
| JP | 2002-512086 | 4/2002 |
| JP | 2004-358107 | 12/2004 |
| JP | 4315489 B2 | 8/2009 |
| JP | 2014066923 A | 4/2014 |
| JP | 2013-192953 | 9/2018 |
| KR | 10-1614939 | 4/2016 |
| KR | 10-1784213 | 10/2017 |
| WO | WO 1993/015648 | 8/1993 |
| WO | 0904725 | 9/2005 |
| WO | WO 2006/073676 | 7/2006 |
| WO | WO 2012/027581 | 3/2012 |
| WO | WO 2014/031192 | 2/2014 |
| WO | WO 2015/142720 | 9/2015 |
| WO | WO 2017/040692 | 3/2017 |
| WO | WO 2017/147605 | 8/2017 |
| WO | WO 2021/144778 | 7/2021 |
| WO | WO 2021/161228 | 8/2021 |
| WO | WO 2022/003569 | 1/2022 |
| WO | WO 2023/026257 | 3/2023 |
| WO | WO 2023/053042 | 4/2023 |

OTHER PUBLICATIONS

China App. CN 201980038145.1, Office Action with Search Report (dated Jun. 23, 2022).
China App. CN 201980038145.1, Reply to Office Action (dated Nov. 8, 2022).
China App. CN 201980038145.1, Office Action (dated Nov. 17, 2022).
China App. CN 201980038145, Office Action (dated Feb. 14, 2023).
EPO App. EP 19746152.8, Communication pursuant to Article 94(3) EPC (dated Sep. 28, 2021).
EPO App. EP 19746152.8, Reply to Communication pursuant to Article 94(3) (dated Feb. 7, 2022).
EPO App. EP 19746152.8, Extended European Search Report (dated Dec. 21, 2022).
EPO App. EP 19746152.8, Communication pursuant to Article 94(3) EPC (dated Mar. 17, 2023).
Japan App. 2020-567600, Office Action (dated Mar. 7, 2023).
PCT/IB2021/050359, ISA/210 International Search Report, and ISA/237 Written Opinion of the International Searching Authority (dated May 18, 2021).
PCT/IB2021/050359, Article 34 Amendment (excerpts) (dated Nov. 18, 2021).
PCT/IB2021/050359, International Preliminary Report on Patentabilty (Chapter II) (dated Mar. 4, 2022).
PCT/IB2021/055823, ISA/210 International Search Report and ISA/237 Written Opinion (dated Aug. 10, 2021).
PCT/IB2021/055823, Article 34 Amendment (dated Mar. 30, 2022).
PCT/IB2021/055823, Written Opinion (dated May 16, 2022).
PCT/IB2022/054938, International Search Report and Written Opinion of the International Searching Authority (dated Nov. 29, 2022).
PCT/IB2022/058030, ISA/210 Search Report and ISA/237 Written Opinion of the International Searching Authority (dated Dec. 19, 2022).
PCT/IB2022/058030, Article 34 Amendment (dated Mar. 19, 2023).
PCT/IB2022/059262, ISA/210 International Search Report and ISA/237 Written Opinion of the International Searching Authority (dated Dec. 14, 2022).
Adaptive Surface Technologies, Inc., AST has brought two distinct product groups to market, https://adaptivesurface.tech (retrieved May 21, 2021).
Eduardo Martín Arranz, María Dolores Martín Arranz, Tomás Robredo, Pablo Mancheño-Corvo, Ramón Menta, Francisco Javier Alves, Jose Manuel Suárez de Parga, Pedro Mora Sanz, Olga de la Rosa, Dirk Büscher, Eleuterio Lombardo, and Fernando de Miguel: Endoscopic submucosal injection of adipose-derived mesenchymal stem cells ameliorates TNBS-induced colitis in rats and prevents stenosis, Stem Cell Research & Therapy 9:95, doi: 10.1186/s13287-018-0837-x (Apr. 10, 2018).
Felix Asche, Basler AG, White Paper, Modern CMOS Sensors and Their Use in Fluorescence-Based Applications (Nov. 2017).
Harvard University, Hansjörg Wyss Institute for Biologically Inspired Engineering at Harvard University, *TLP: A Non-Stick Coating for Medical Devicesz*, https://wyss.harvard.edu/technology/tlp-a-non-stick-coatng-for-medicai-devices (retrieved May 21, 2021).
Martin J. Hoogduijn, Eleuterio Lombardo, Concise Review: Mesenchymal Stromal Cells Anno 2019: Dawn of the Therapeutic Era? Stem Cells Translational Medicine 00:1-9 doi: 10.1002/sctm.19/0073 (2019).
Oksana Kehoe, Alison Cartwright, Ayman Askari, Alicia J El Haj, and Jim Middleton: Intra-articular injection of mesenchymal stem cells leads to reduced inflammation and cartilage damage in murine antigen-induced arthritis, Journal of Translational Medicine 12:157, doi:10.1186/1479-5876-12-157 (Jun. 3, 2014).
Matthew J. Kraeutler, Tigran Garabekyan, Omer Mei-Dan, The use of platelet-rich plasma to augment conservative and surgical treatment of hip and pelvic disorders, Muscles, Ligaments and Tendons Journal 410 2016;6 (3):409-419 doi: 10.11138/mltj/2016.6.3.410 (Dec. 21, 2016).
Benedetta Mazzanti, Bruno Lorenzi, Annalisa Borghini, Margherita Boieri, Lara Ballerini, Riccardo Saccardi, Elisabetta Weber, and Federica Pessina: Local injection of bone marrow progenitor cells for the treatment of anal sphincter injury: in-vitro expanded versus minimally-manipulated cells, Stem Cell Research & Therapy 7:85, doi 10.1186/s13287-016-0344-x (Jun. 21, 2016).
Raffy Mirzayan, Joseph D. Cooper, and Jorge Chahla, Carbon Dioxide Insufflation of the Knee in the Treatment of Full-Thickness Chondral Defects With Micronized Human Articular Cartilage, Arthroscopy Techniques, 7:10:e969-e973, doi: 10.1016/j.eats.2018.05.005 (Oct. 2018).
NanoSurgery Technology Corp., Product Technology, Introducing the NanoScope, http://nanosurgerytech.com/product-technology/ (accessed Sep. 15, 2019).
Steffi Sunny, George Cheng, Daniel Daniel, Peter Lo, Sebastian Ochoa, Caitlin Howell, Nicolas Vogel, Adnan Majid, Joanna Aizenberg, Transparent antifouling material for improved operative field visibility in endoscopy, Proceedings of the National Academy of Sciences U.S.A., Oct. 18, 2016;113(42):11676-11681. doi: 10.1073/pnas.1605272113 (Sep. 29, 2016).
Trice Medical, Mi-eye 2 is the revolutionary alternative to a traditional MRI, https://tricemedical.com/mi-eye/ (accessed Jul. 25, 2019).
Rene von Fintel, Basler AG, White Paper, Modern CMOS Cameras as Replacements for CCD Cameras (May 2018).

* cited by examiner

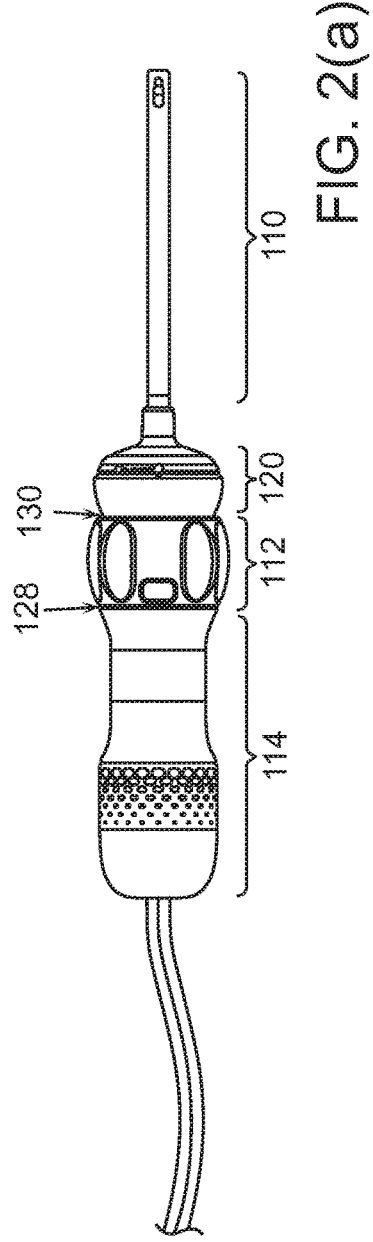
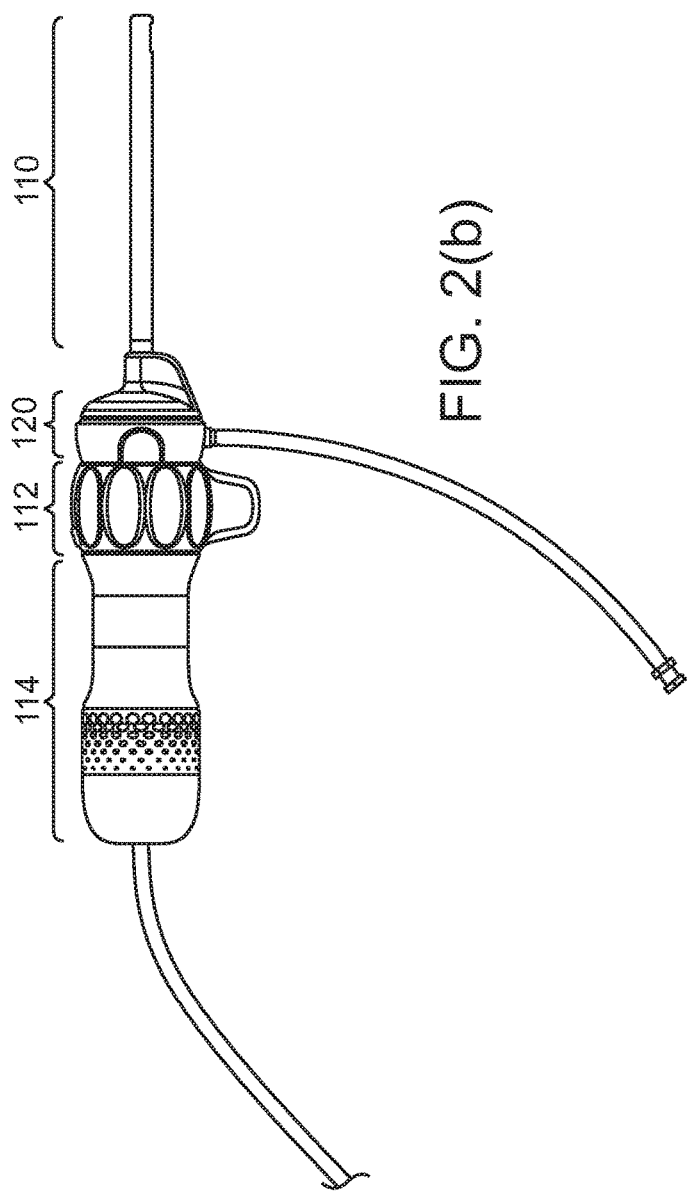
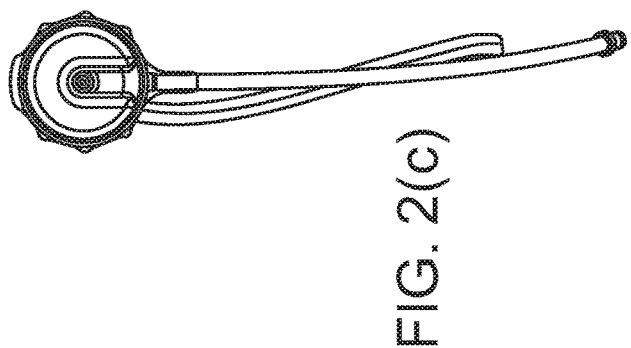

ENDOSCOPE FOR IMAGING IN NONVISIBLE LIGHT

This application claims priority, as a non prov. of provisional of U.S. Provisional Application Ser. No. 62/841,163, filed Apr. 30, 2019, titled "Endoscopes with Disposable Camera Shaft and for Imaging in Nonvisible Light". The entire disclosure of the '163 application, of U.S. Provisional application 62/682,585, filed Jun. 8, 2018, and 62/722,150, filed Aug. 23, 2018, both titled "Endoscope with Disposable Camera Shaft," are incorporated by reference.

BACKGROUND

This application relates to endoscopes, laparoscopes, arthroscopes, colonoscopes, and similar apparatus, instruments, implements, or processes specially adapted or intended to be used for evaluating, examining, measuring, monitoring, studying, or testing living or dead human and animal bodies for medical purposes.

SUMMARY

In general, in a first aspect, the invention features an endoscope. One or more image sensors are designed to capture image data in visible light. One or more image sensors are designed to capture image data in a nonvisible portion of the electromagnetic spectrum. An insertion shaft is designed to support the one or more visible and nonvisible image sensors at or near a distal tip with sufficient rigidity to permit guidance to a surgical site in a human body. Image processing software trained through machine learning to enhance image quality of at least the nonvisible portion of the image, and to present the enhanced nonvisible image as a real-time, visible presentation to a surgeon.

Embodiments of the invention may include one or more of the following features. The software may be programmed to display the visible presentation of the nonvisible image as a split-screen display with the visible light image data. The software may be programmed to display the visible presentation of the nonvisible image overlaid or merged with the visible light image data. The software may be programmed to overlay or merge the nonvisible image with the visible light image data by registering for parallax differences. The software may be programmed to overlay or merge the nonvisible image with the visible light image data by recovering three-dimensional spatial relationships. An ultraviolet or infrared LED may be mounted within the endoscope to illuminate tissue in the field of view of the nonvisible image sensor. The one or more image sensors may be designed to capture image data in visible light and the one or more image sensors designed to capture image data in a nonvisible portion of the electromagnetic spectrum are designed into a single image plane. An electronic shutter may chop for alternate illumination between multiple illumination sources of differing wavelength or alternate sensing between image sensors of differing wavelength sensitivity. A strobe circuit may chop for alternate illumination between multiple illumination sources of differing wavelength.

The one or more image sensors designed to capture image data in visible light, the one or more image sensors designed to capture image data in a nonvisible portion of the electromagnetic spectrum, and image processing software are designed to capture image data from tissue below a surface at the field of view of the image sensors.

The one or more image sensors designed to capture image data in visible light and the one or more image sensors designed to capture image data in a nonvisible portion of the electromagnetic spectrum and image processing software are designed to capture image data from tissue below a surface at the field of view of the image sensors. Tissue in the field of view of the nonvisible image sensor may be infused with contrast fluorescent dye.

The above advantages and features are of representative embodiments only, and are presented only to assist in understanding the invention. It should be understood that they are not to be considered limitations on the invention as defined by the claims. Additional features and advantages of embodiments of the invention will become apparent in the following description, from the drawings, and from the claims.

DESCRIPTION OF THE DRAWINGS

FIGS. 2(a), 2(b), and 2(c) are plan views of endoscopes.

DESCRIPTION

Figure 1A:
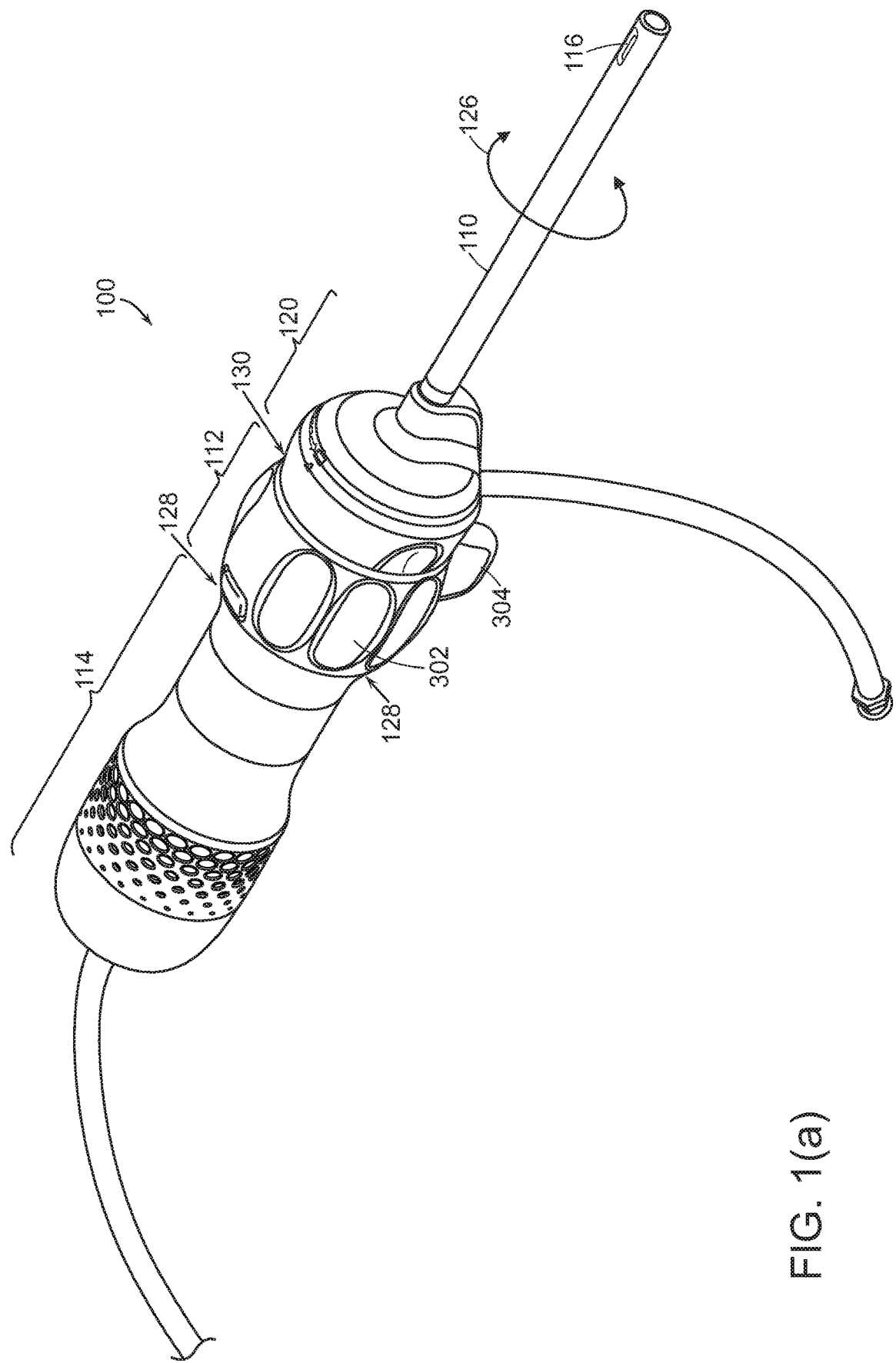
FIGS. 1(a), 1(b), 1(c), 1(d), 2(d), 3(a), 3(f), 3(h), 4(a), and 5(a), 5(b), and 5(d) are perspective views of endoscopes.

The Description is organized as follows.

I. Overview

II. Reposability: partially reusable, partially disposable/replaceable, and a coupling joint between III. Surgical Imaging Combining Visible and Nonvisible Light III.A. Imaging sensors for nonvisible light III.B. Illumination and contrast for nonvisible imaging III.C. Image processing IV. Additional features of an endoscope V. Other embodiments

I. Overview

Referring to FIGS. 1(a), 1(b), 1(c), and 1(d), a surgical endoscope 100 may be structured to permit detachment of a shaft 110 portion from the endoscope's handle 112, 114. A camera or image sensor at tip 116 of the shaft, any panning mechanism, illumination, power and signal connectors, and fluid flow channels may be in the disposable shaft 110. Handle 112, 114 may be designed to be reusable (which implies that handle 112, 114 may be sterilizeable, for example in an autoclave or other sterilization device, or protectable by a disposable sterility sleeve). Joint 130 between the detachable shaft and the reusable parts of handle 112, 114 may be generally distal in the handle (but not necessarily at the distal-most end). The replaceable shaft portion 110 may be disposable, along with a disposable portion 120 of the handle that is disposable with shaft 110.

II. Reposability: Partially Reusable, Partially Disposable/Replaceable, and a Coupling Joint Between Referring to FIGS. 1(a), 1(c), 2(a), 2(b), 2(c), 2(d), and 3(a), the handle of the endoscope 100 may include three principle components:

- The disposable cap 120. This distal-most portion of the handle may serve as a mounting base for shaft 110, and may disconnect from the remainder 112, 114 of the handle. This disposable cap portion 120 (along with shaft 110 and componentry inside) may be disposable.
- Rotation collar 112 may have surface features 302, 304 to allow a surgeon to rotate the rotation collar 120 about the central axis of the handle, that is, about the roll axis 126 of the shaft. During surgery, insertion shaft 110, disposable cap 120 and rotation collar 112 may be locked to rotate with each other, so that rotating the rotation collar effects rotation 126 of the disposable cap 120 and shaft 110.
- Proximal stationary handle 114 has a shell surrounding componentry within the handle. The outer diameter and outer surface of handle 114 may be designed to provide an easy and low-slip grip for a surgeon's hand. Joint 128 between the proximal handle and rotation collar may allow these two components to rotate relative to each other. In some cases, a circuit board and similar componentry inside proximal handle 114 may rotate with disposable cap 120 and rotation collar 112, inside proximal handle 114.

Disposable cap 120 and rotation collar 112 may be separable from each other at joint 130, so that disposable cap 120 and shaft 110 may be disposable, while handle 114 and rotation collar 112 (and componentry inside them) are reusable.

Referring to FIGS. 1(a), 1(c), 1(d), and 3(a), between the disposable cap 120 and rotation collar 112, three basic connections may be made:

- A rotation-locking coupling 140, 142 to hold the disposable portion 120 to the reusable handle 112, 114. Coupling 140, 142 may have sufficient strength to transmit insertion and withdrawal forces, roll, pitch, and yaw torques, lateral forces, and similar forces from the proximal reusable handle 112, 114 to the distal disposable portion 120 and shaft 100, thereby to allow a physician to aim the illumination and/or camera as needed. Joint 130 between disposable cap 120 and rotation collar 112 may lie generally toward the distal end of the handle. The disposable cap and rotation collar 112 may engage through flat force-transmittal surfaces 144 at the center of joint 130 and around the circumferences, so that these forces are supported around the circumference of separable joint 130. One or more release buttons 146 may be pressed or squeezed to cause one or more locking snaps 148 to disengage. The mechanical connection may include a rotatable locking ring or other release/fixation mechanisms.
- An electrical connection to supply power to the illumination source and camera, and to carry optical signals back from the camera to the processing board in handle 112, 114 and display system outside the endoscope. The disconnectable electrical connections for power and signal may be effected by a USB-C connector 150, 152, mini HDMI connector, or similar connector that can maintain signal integrity for high speed signals. If illumination is conveyed by optical fiber, joint 130 may include an optical connector.
- A disconnectable connection to any panning mechanism for the camera may be effected by a physical connector, such as a linkage.

In some cases, the camera/image sensor, LED, and electronic connections (and any mechanical connections for panning the camera/image sensor) may be removable from insertion shaft 110. Shaft 110 and cap 120 may be smooth and simple enough in shape to allow easy sterilization. Similarly, once the electronics are removed from interior of shaft 110, they may be sterilizeable as well. it may be cost-effective, especially in lower-labor-cost markets, to disassemble, sterilize, and reassemble the shaft and its interior components for reuse.

Figure 5A:
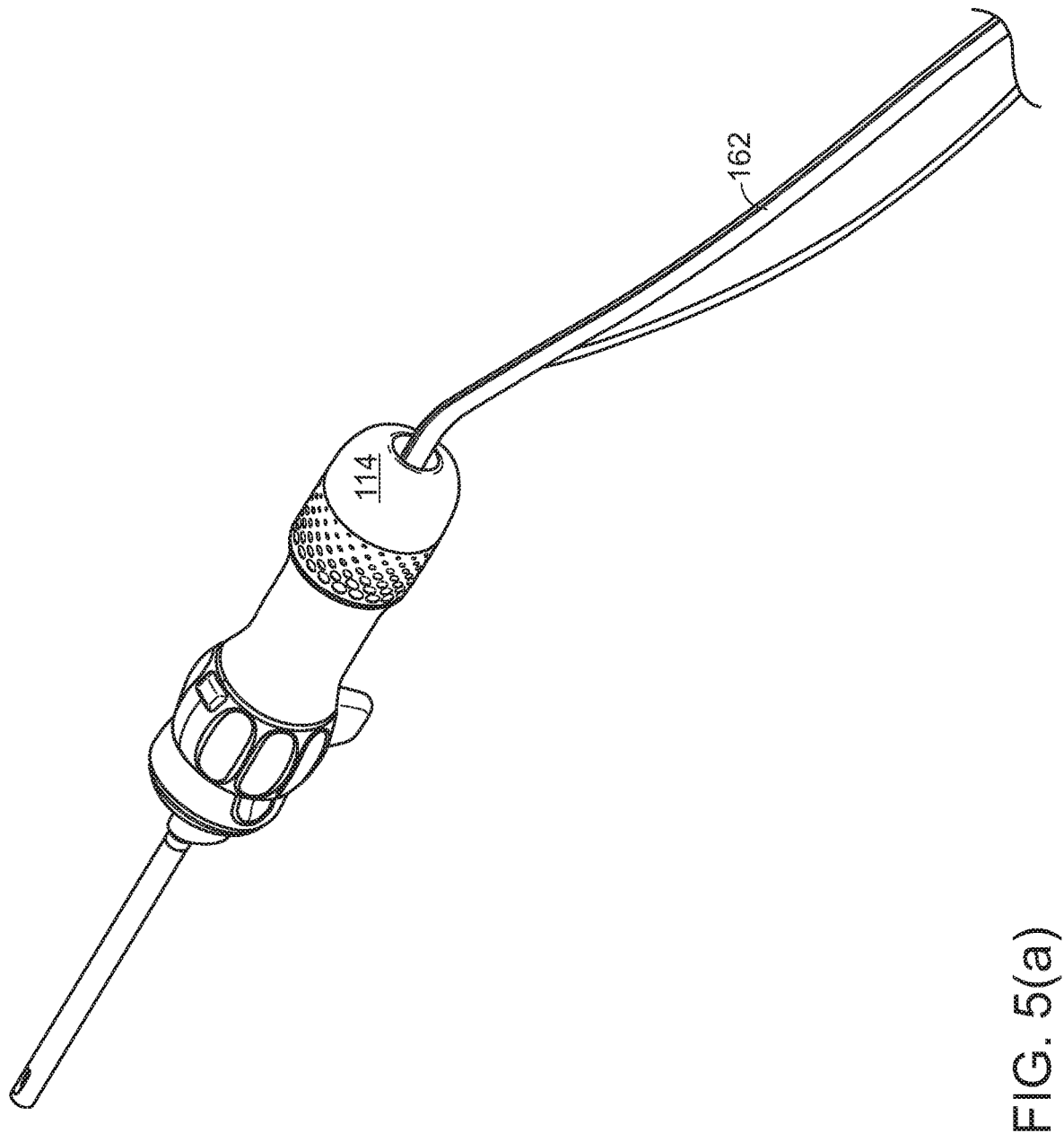
Figure 5B:
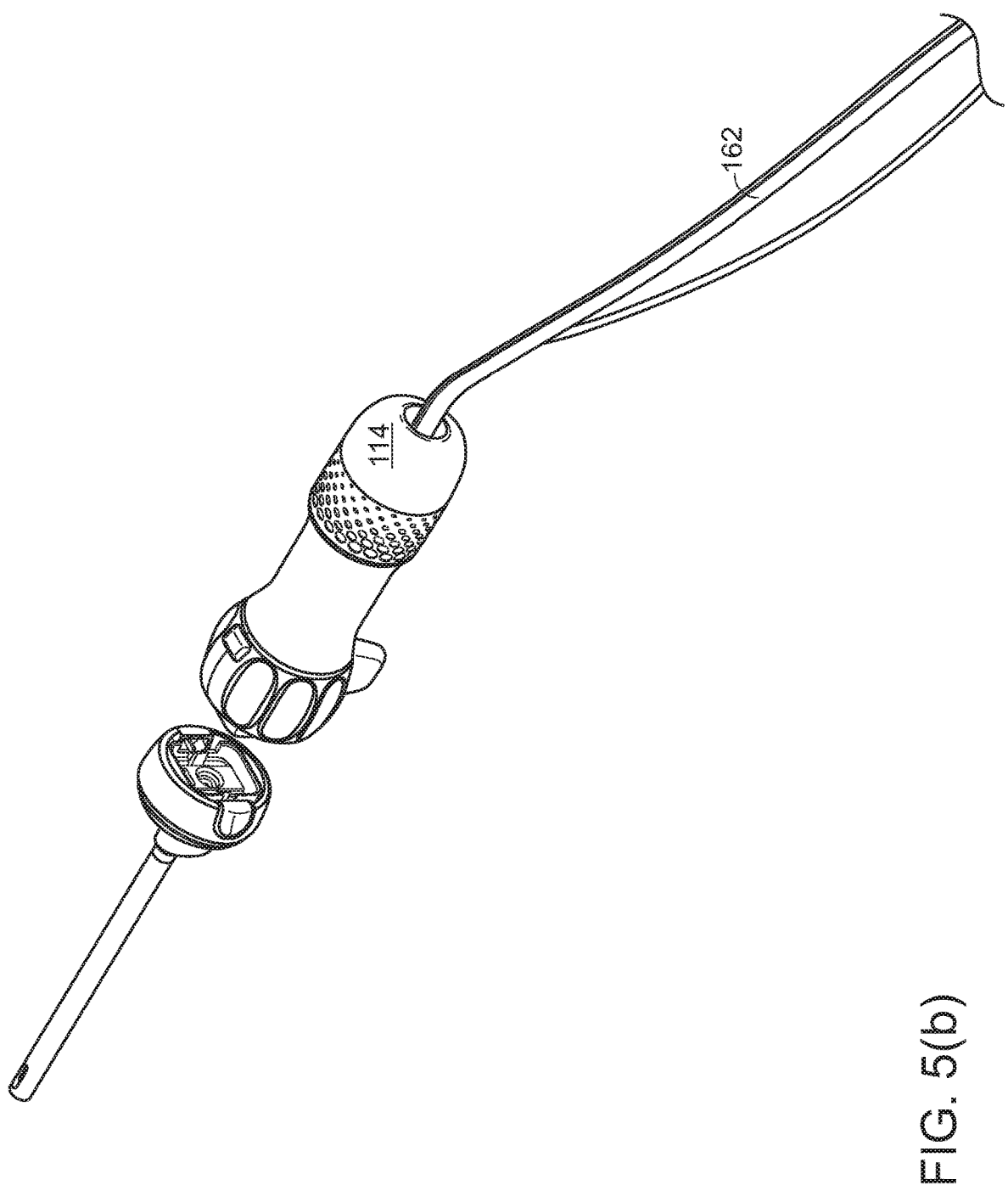

One or more fluid hoses 160 for irrigation liquid or inflation gas (or two hoses, one for fluid and one for gas) may enter through disposable cap 120, so that the entire set of fluid tubing for the irrigation/inflation channel may be disposable with the disposable shaft portion. In other cases (e.g., FIGS. 5(a) and 5(b)), a fluid hose 162 may enter the proximal end of the scope, and disconnectable fluid connections within joint 130 for fluid inflow and outflow may be effected by gaskets, O rings, and the like. Alternatively, connectors for the hoses may be outboard of the endoscope itself, either near the endoscope (for applications where it may be desirable to allow "quick change" replacement of the insertion shaft in the course of a single procedure), or far from the endoscope, typically at the receptacle for waste fluid, to ease disposal of all hoses that are potentially contaminated by contact with the patient.

Disposable shaft 110, 120 may be designed to facilitate disposability of components that come into contact with bodily fluids. Because sterilization is often imperfect, patient safety may be improved by disposing of components that have come into contact with patient bodily fluids. To improve sterilizability, it may desirable to reduce componentry in the disposable component 110, 120 so that cost of the disposable component may be reduced, and to reduce surface features and crevices that may be difficult to sterilize. Thus, the lens, image sensor, LED, panning mechanism, and shaft may be disposable. In addition, because shaft 110 is used for fluid inflow and outflow, and is disposable, sealing against bodily fluids may be unnecessary.

Figure 5C:
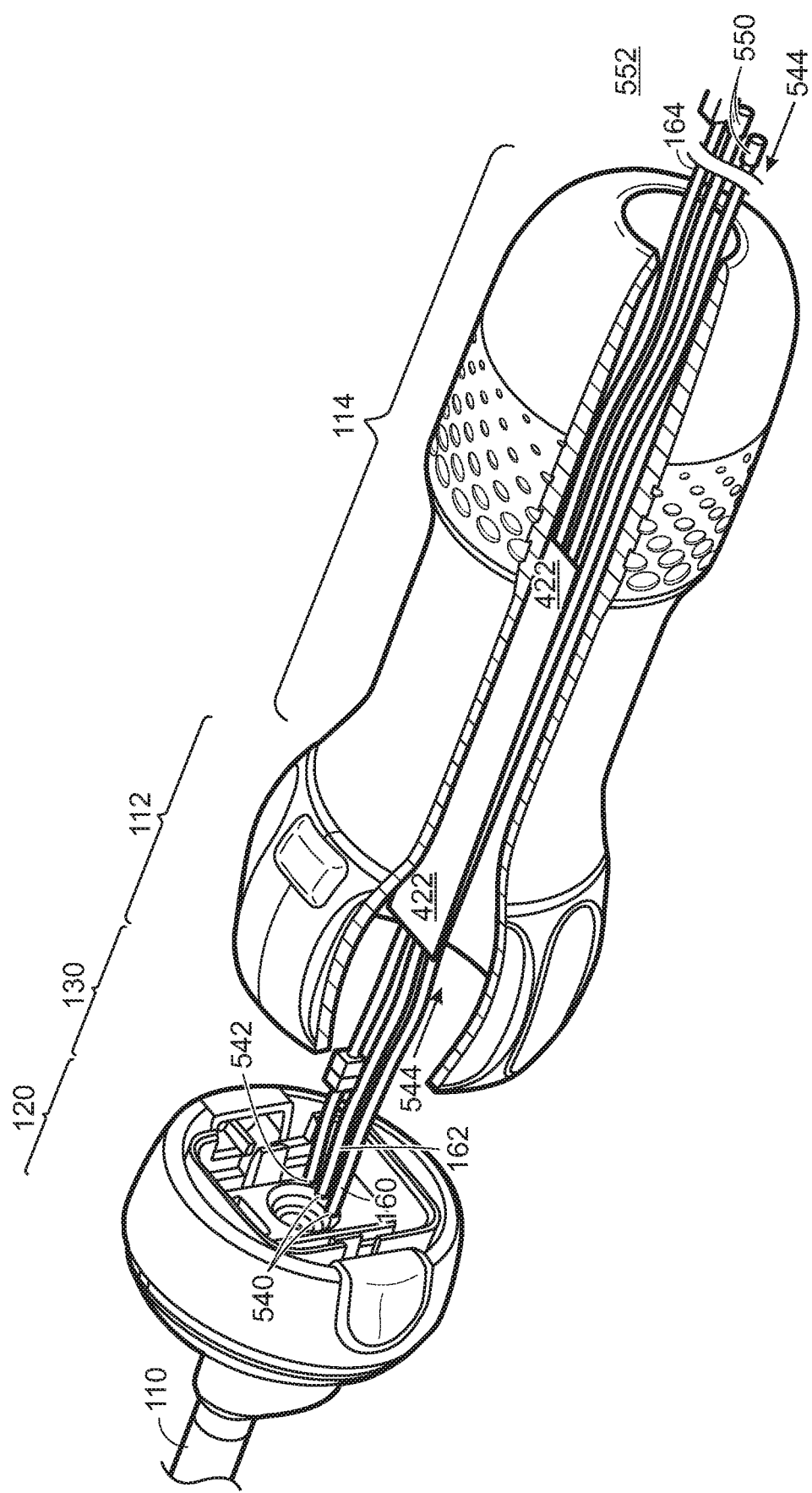

Referring to FIG. 5(c), hoses 160, 162 for irrigation/insufflation fluid/gas in, irrigation/insufflation fluid/gas out, and electrical connection cord 164 may be permanently affixed 540, 542 to disposable cap 120. This arrangement may allow that hose 162 that carries water out of the surgical cavity, and which is therefore contaminated, may be disposable, and no fluid will come into contact with the reusable part 114 of the handle. Hoses and cord 160, 162 may be routed through channel 554 running the length of reusable handle 112, 114. Channel 544 may be of inner diameter large enough to permit easy passage of hoses and cord 160, 162, 164, and connectors 550, 552, and have a continuous smooth wall that permits easy sterilization, to permit ready replacement of the replaceable components. Channel 554 may be off the central axis, to allow printed circuit board 422 to lie on the central axis. Connectors 550, 552 at the end of hoses and cords 160, 162 may be small enough to pass through channel 554. Thus, replacement of shaft 110, cap 120, hoses and cords 160, 162 may be effected by threading connectors 550, 552 and hoses and cord 160, 162 through channel 544. Electrical cord 164 may have a connector 554 at or near joint 130, and hose(s) 160 for irrigation/insufflation fluid/gas flowing into the surgical cavity may likewise have a connector at joint 130 to allow this hose(s) to be reusable, or may be permanently affixed 540 to reduce possibility of leaking. Having hoses and cable 160, 162 roughly on-axis reduces undesirable cable flop as the scope is in use, and reduces undesirable torque on cap 120. Forming shaft 120, cap 120, and hoses 160, 162 as an integral unit for replacement reduces possibility of leaking, and improves sterility of the replacement operation.

Figure 5D:
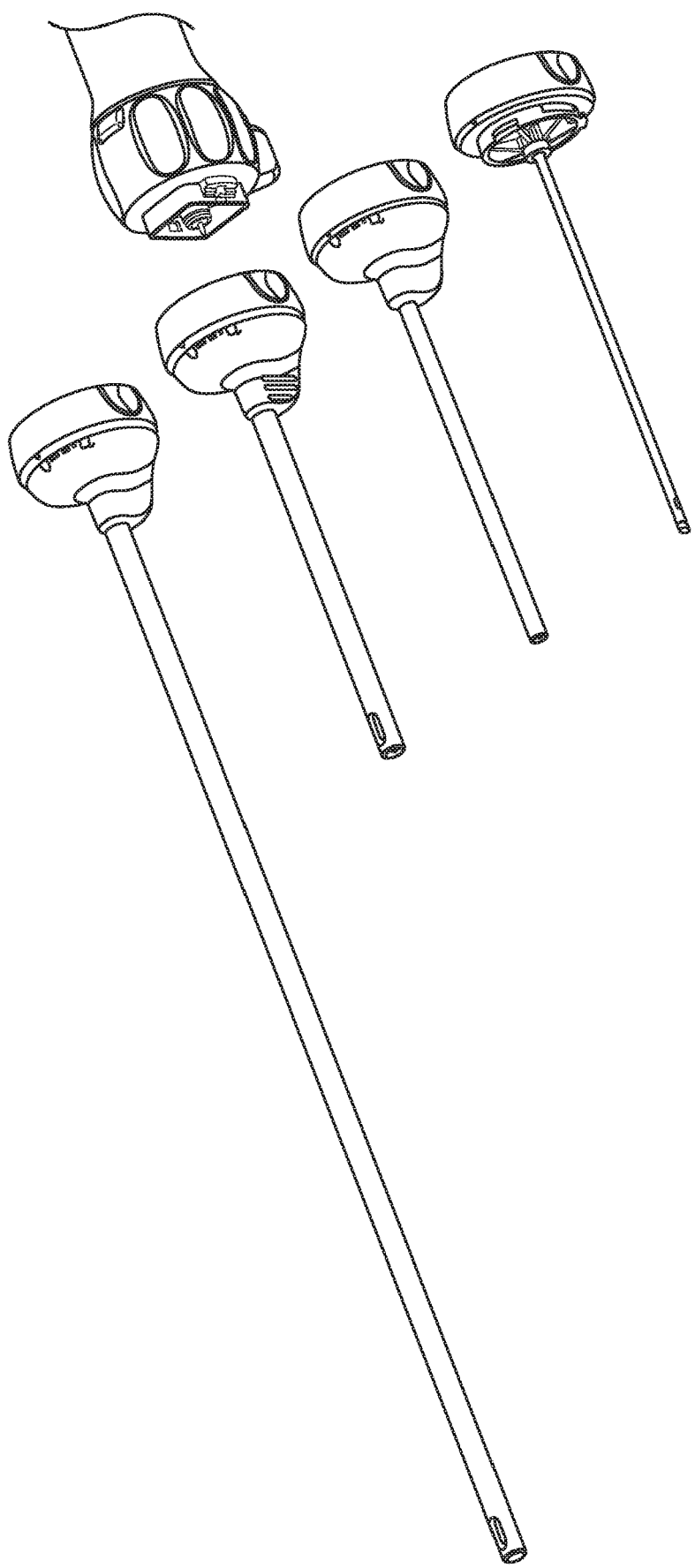

Referring to FIG. 5(d), the replaceable/disposable shaft and its mounting componentry may be specialized to different types of surgery. For example, a replaceable disposable cap/shaft unit 110, 120 for laparoscopic thoracic surgery may have a shaft of 400 mm length and diameter of 10 mm. Replaceable components for arthroscopic surgery of knees and hips may be 155 mm in length, and 5.5 mm or 4 mm in diameter. For small joints, a replaceable shaft of 2.9 mm diameter or less may be preferred. Typical dimensions for various surgical specialties may be as follows (measured in millimeters):

| Scope Type | Discipline | Cannula diameter | | Scope diameter | |
| --- | --- | --- | --- | --- | --- |
| | | Min | Max | Min | Max |
| Arthroscope (small joint) | Arthroscopy | 2.8 | 4.0 | 1.9 | 2.9 |
| Arthroscope (large joint) | Arthroscopy | 4.7 | 6.0 | 2.9 | 5.7 |
| Cytoscope | Cytoscopy | | | 2.9 | 5.7 |
| Encephaloscope | ENT | | | 2.0 | 4.0 |
| Hysteroscope | Gynecology | 3.7 | 7.0 | 2.0 | 5.0 |
| Laparoscope | Laparoscopy | | | 2.0 | 10.0 |
| Sinuscope | ENT | | | 2.0 | 4.0 |
| Thoracoscope | Pulmonary | | | | 10 |

Various replaceable components 110 may have different instruments at tip 116. For example, various replaceable shafts may have cameras oriented at 0° (directly on-axis), 30°, 45°, 70°, and 90°.

Figure 1B:
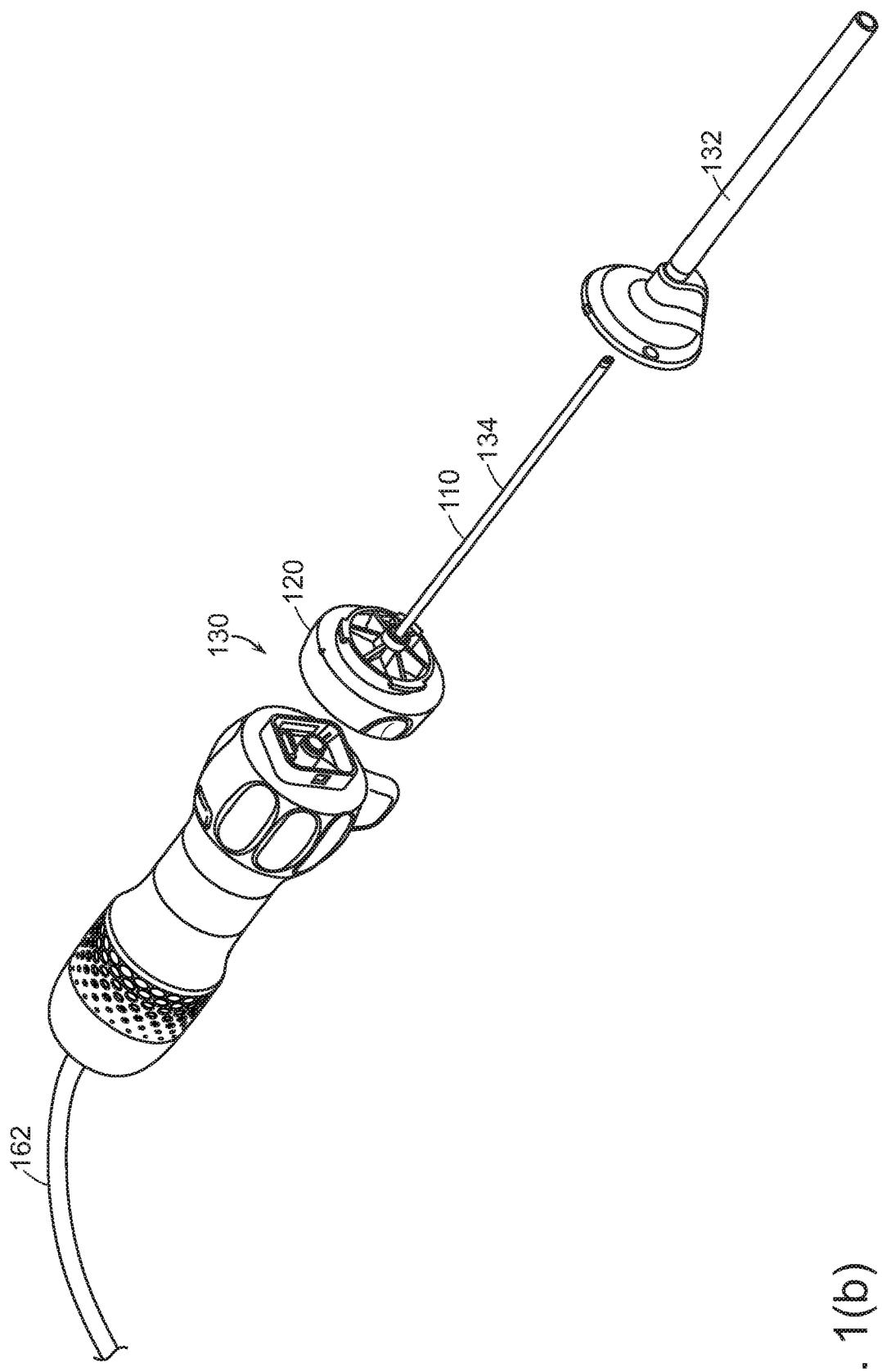
Figure 1C:
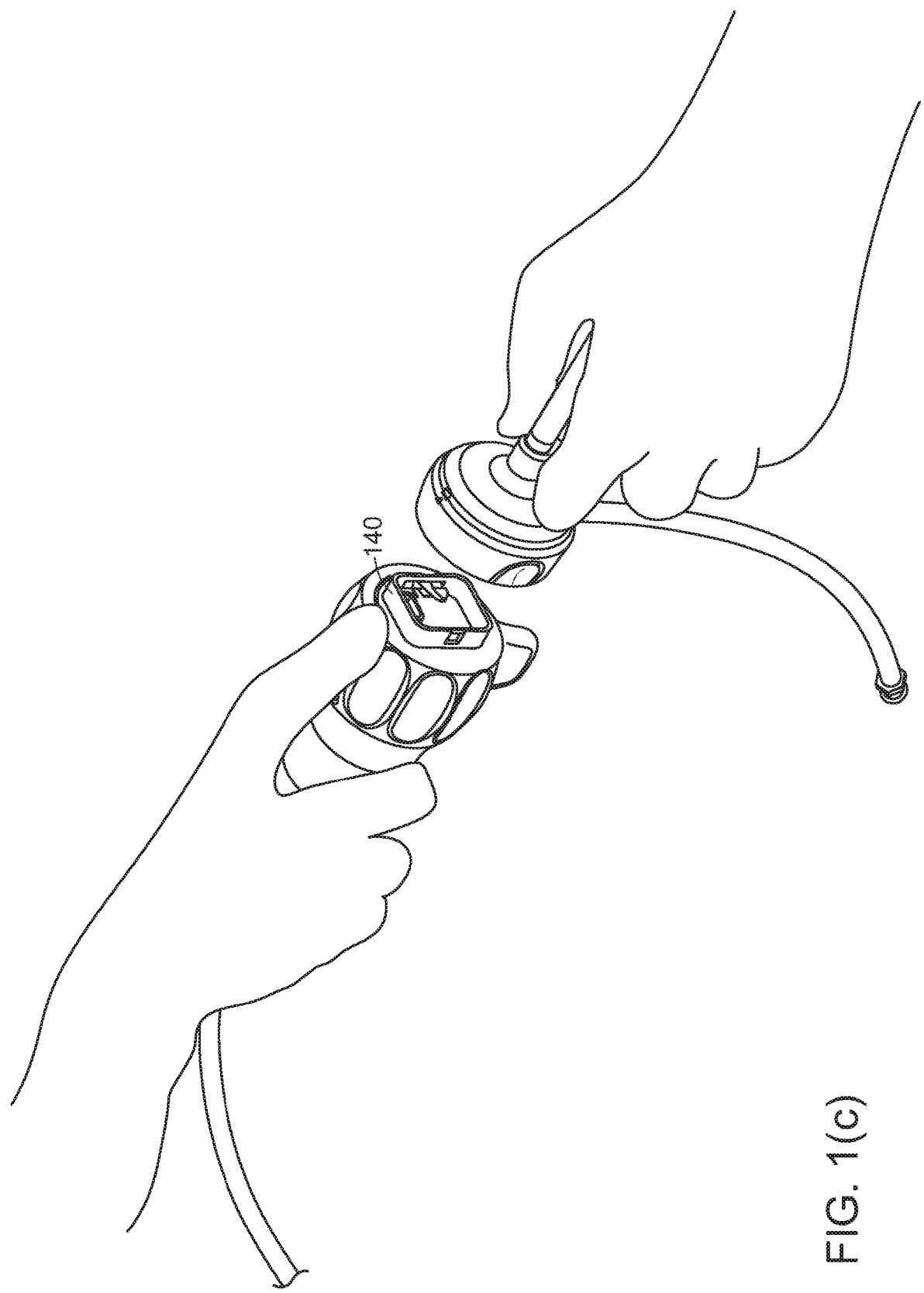
Figure 1D:
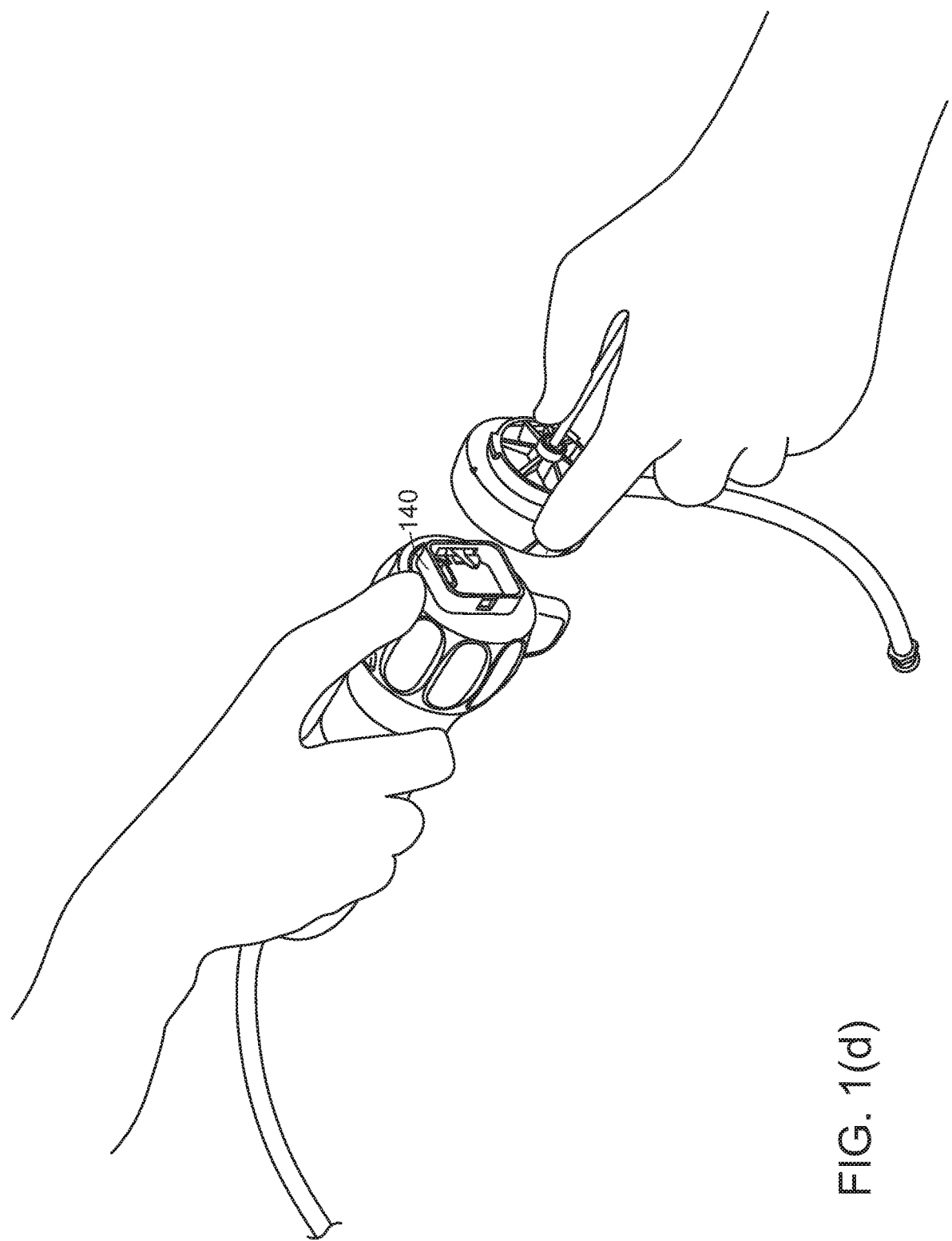
Figure 2D:
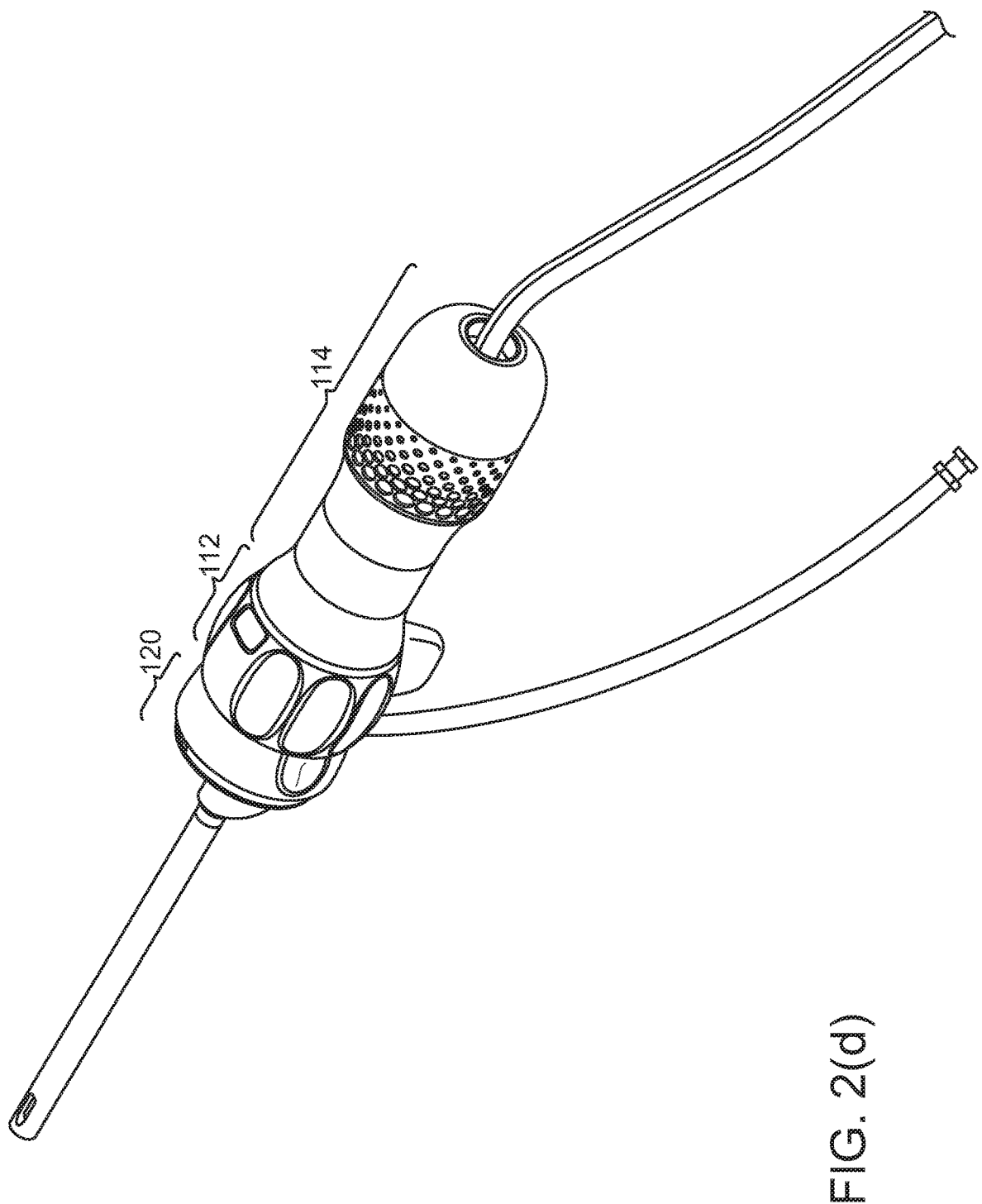
Figure 3A:
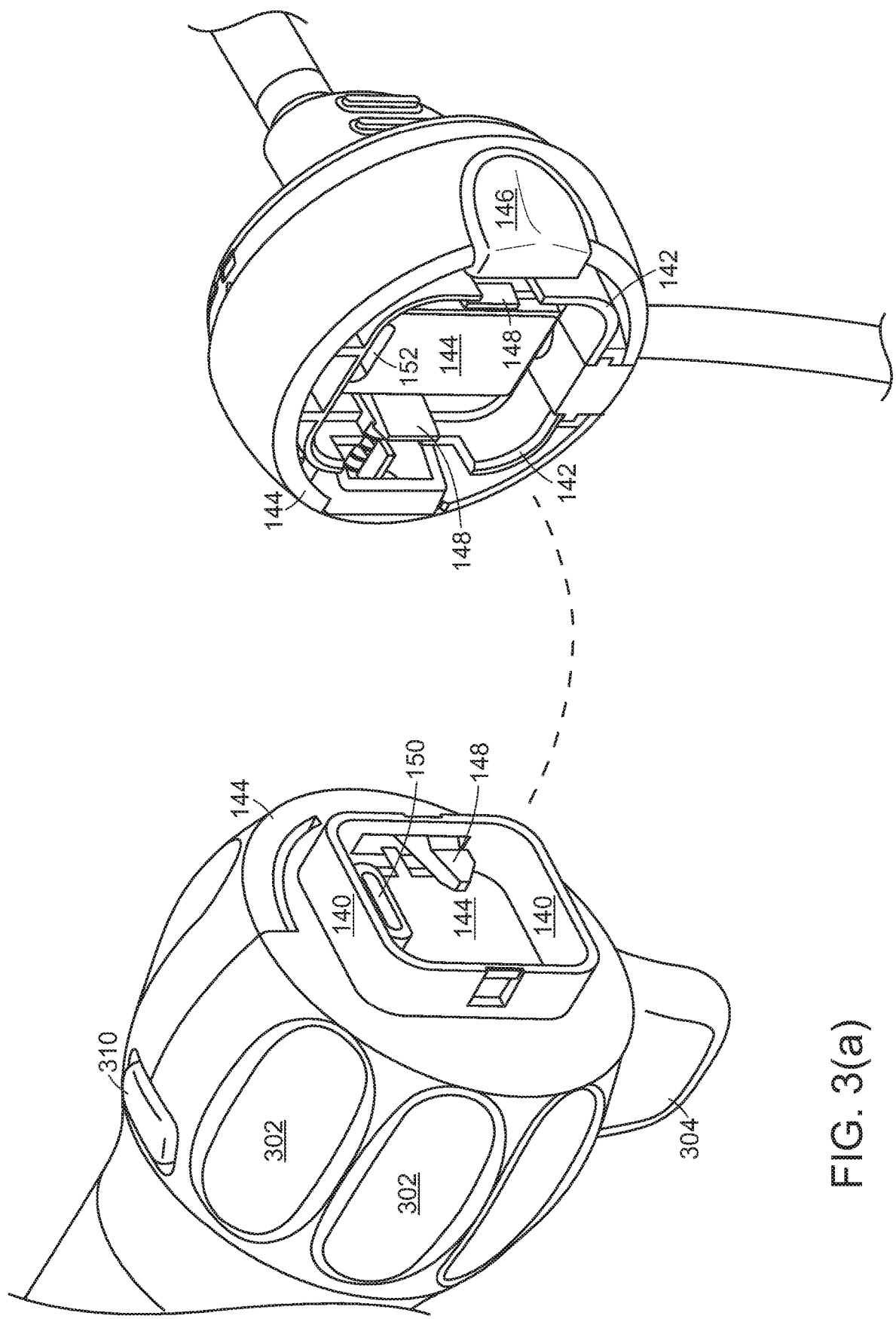
Figure 3B:
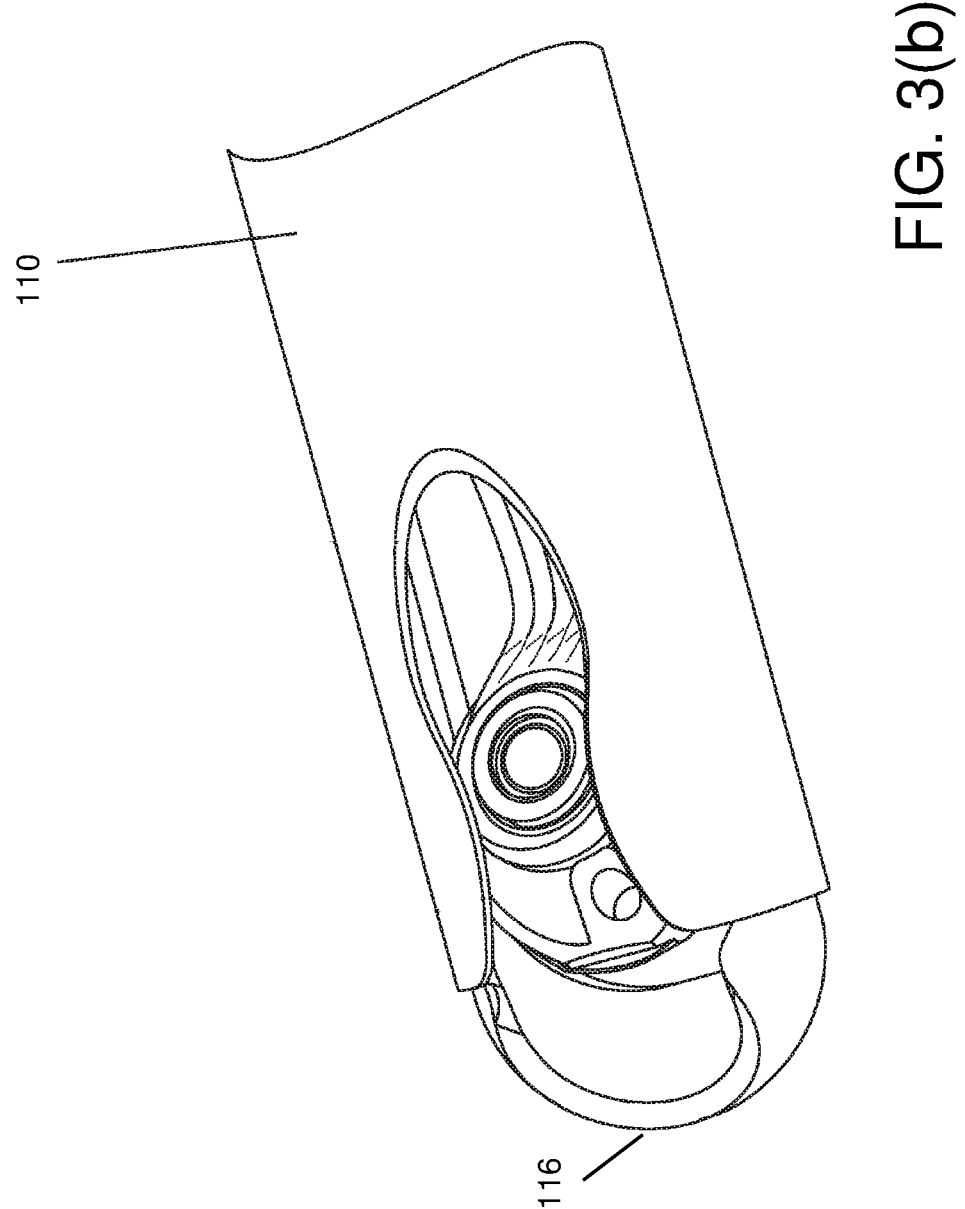
FIGS. 3(b), 3(c), 3(d), 3(e), 3(g), 4(b), 4(c), 4(d), and 5(c) show endoscopes, partially cut away.
Figure 3C:
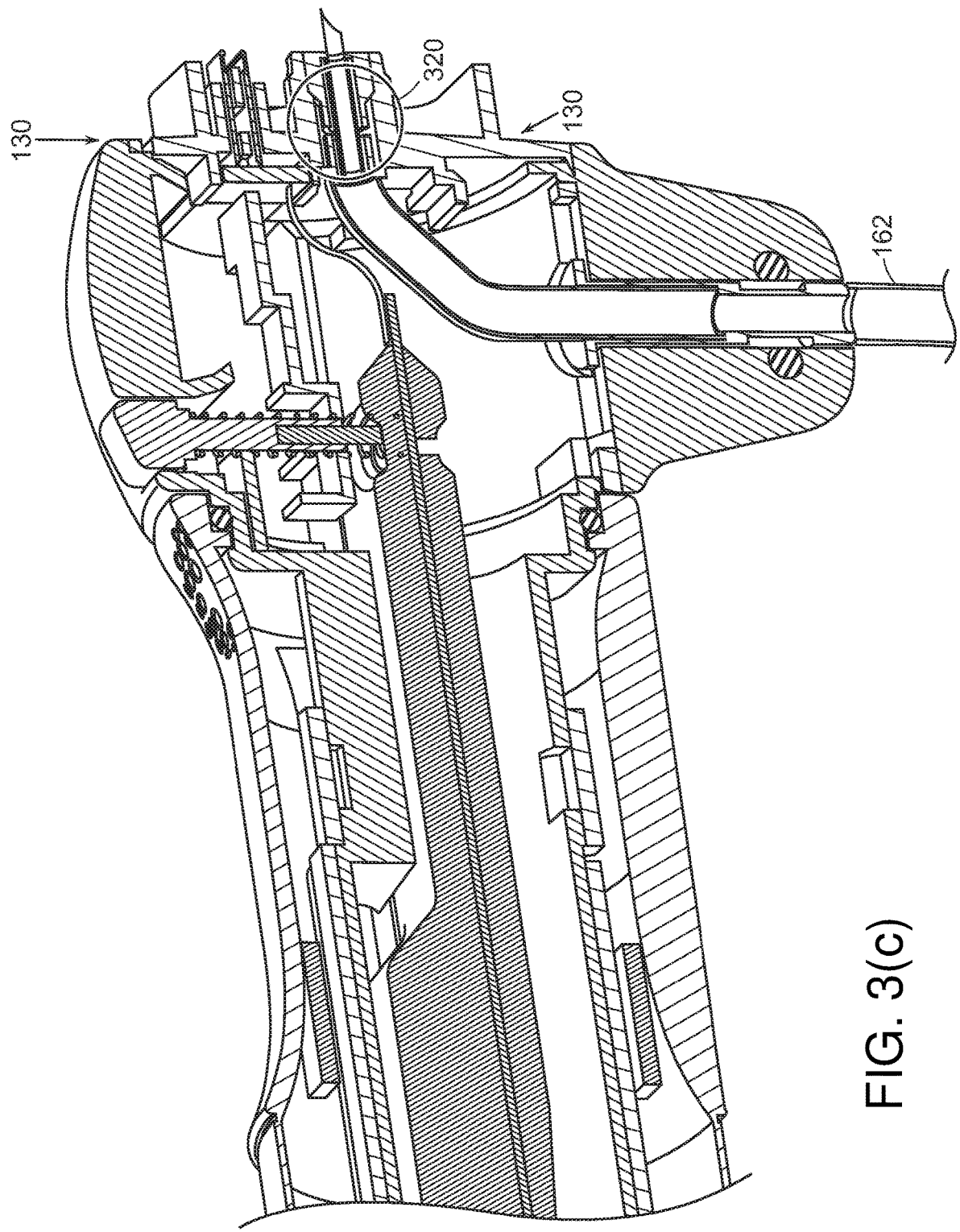
Figure 3D:
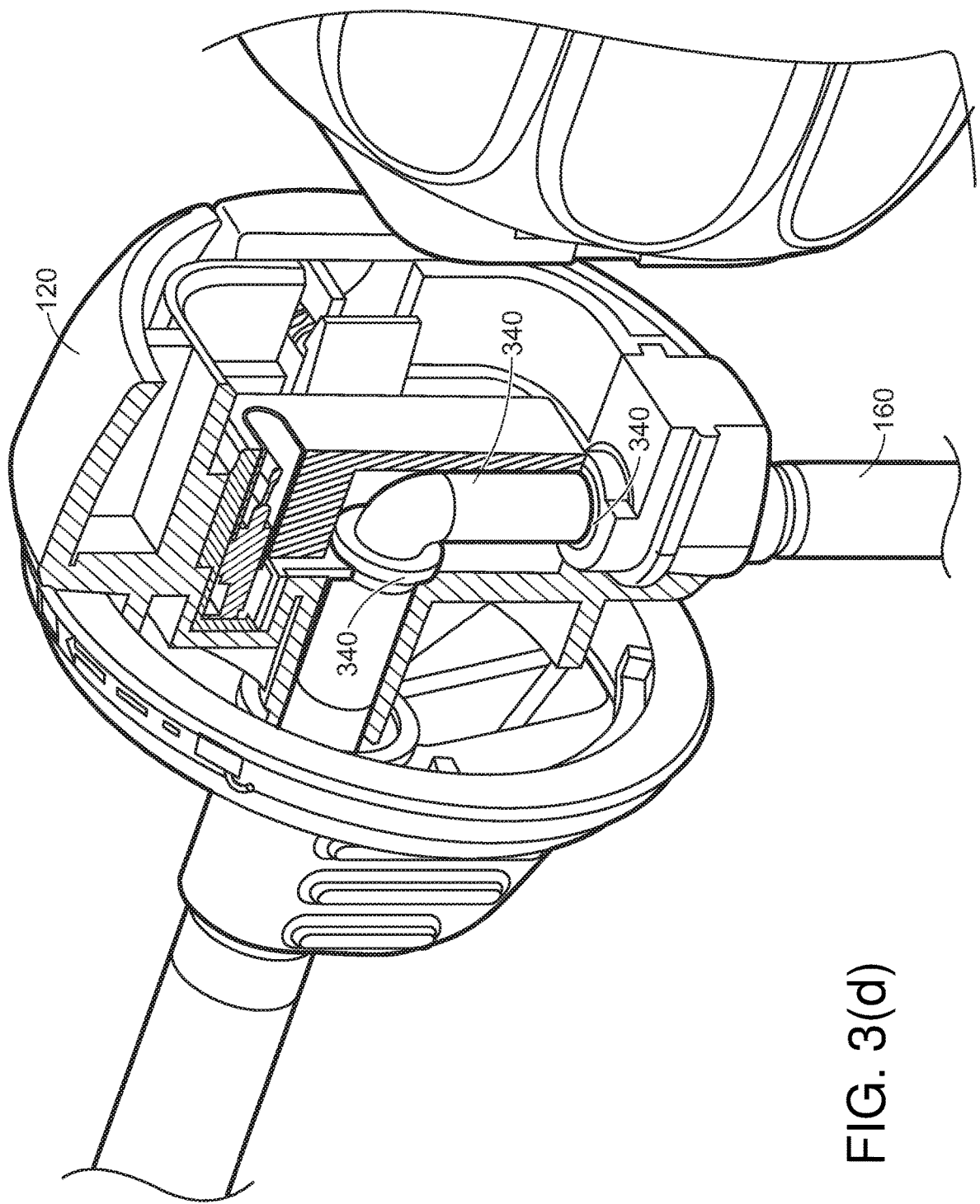
Figure 3E:
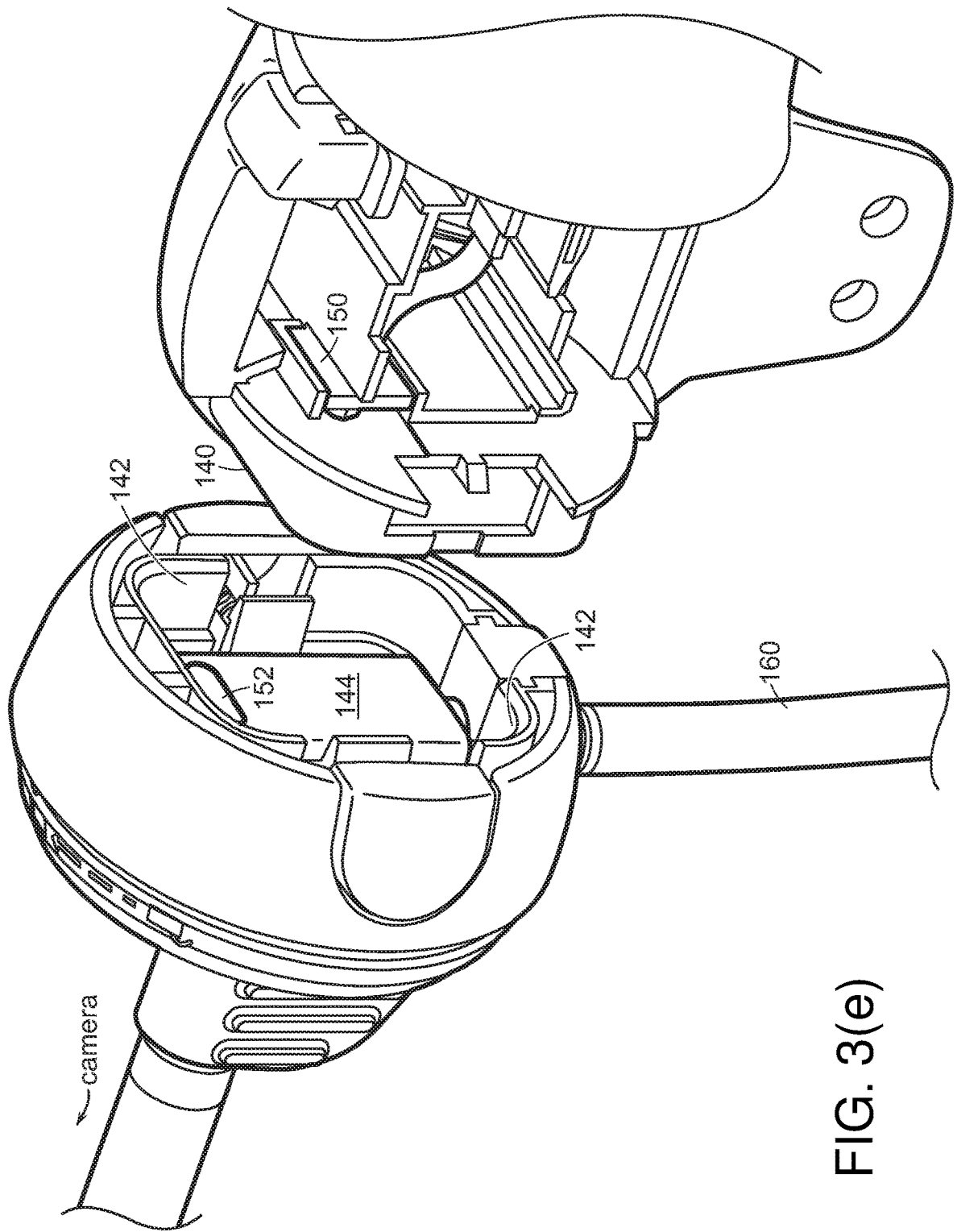
Figure 3F:
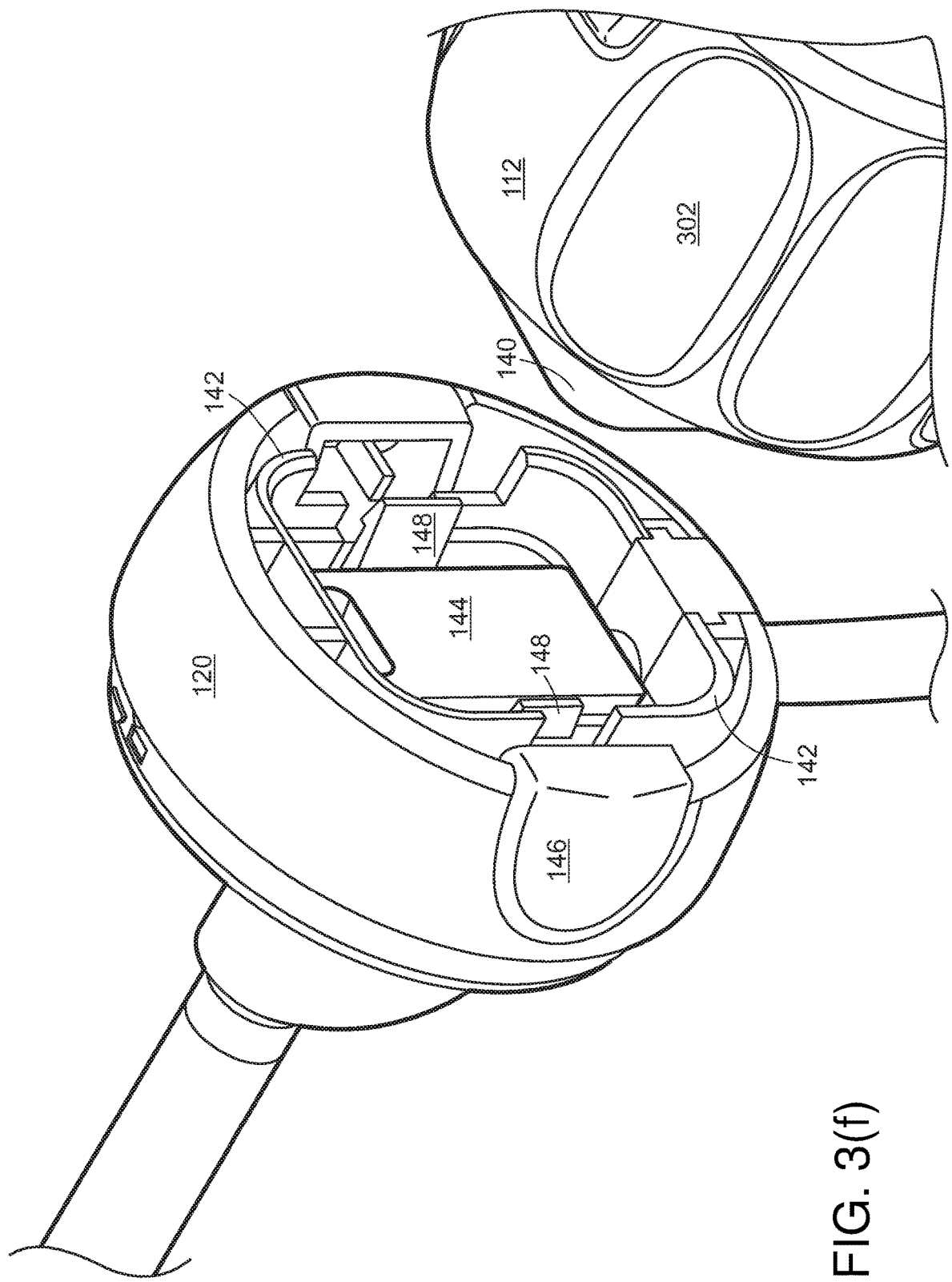
Figure 3G:
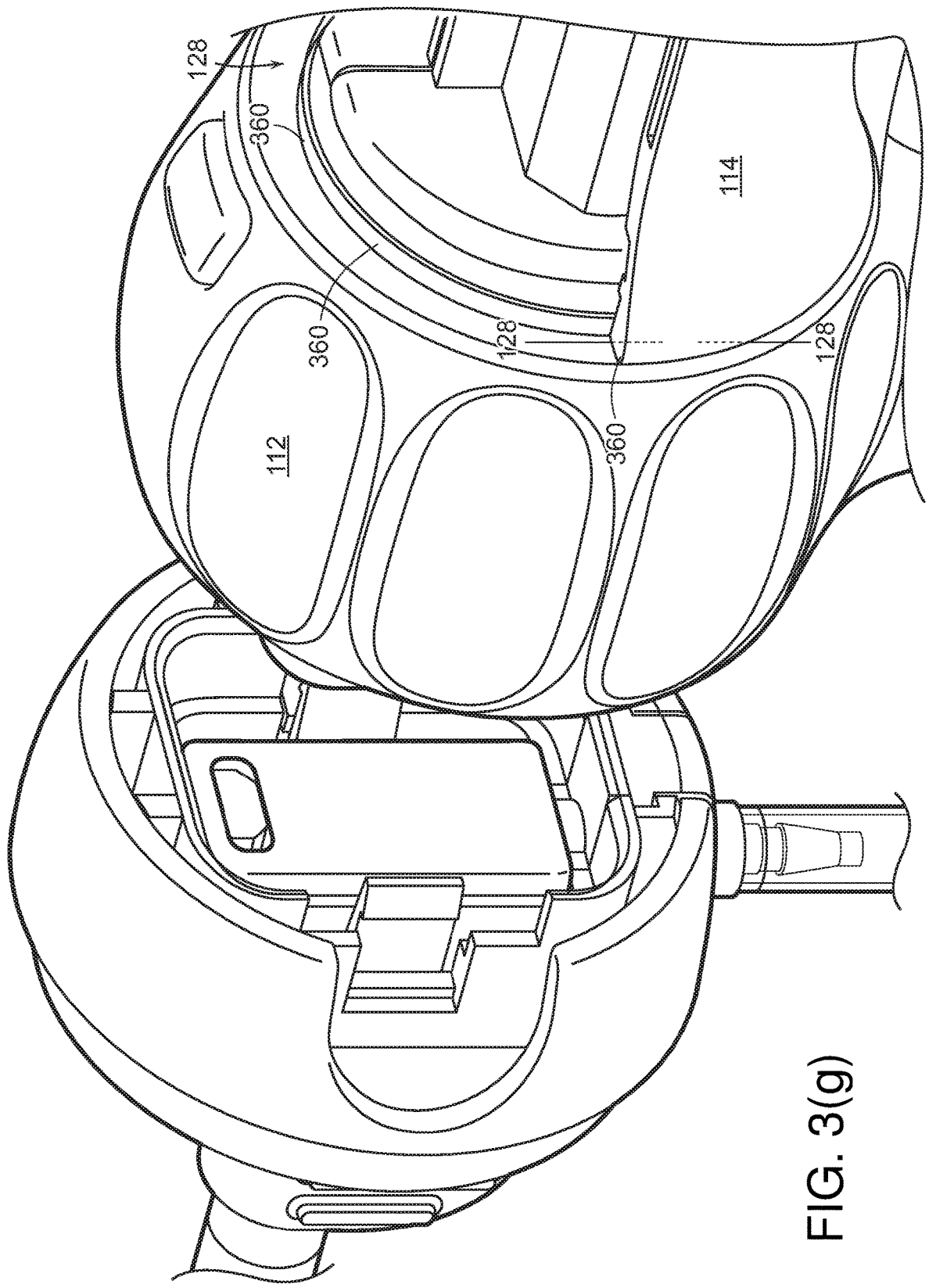
Figure 3H:
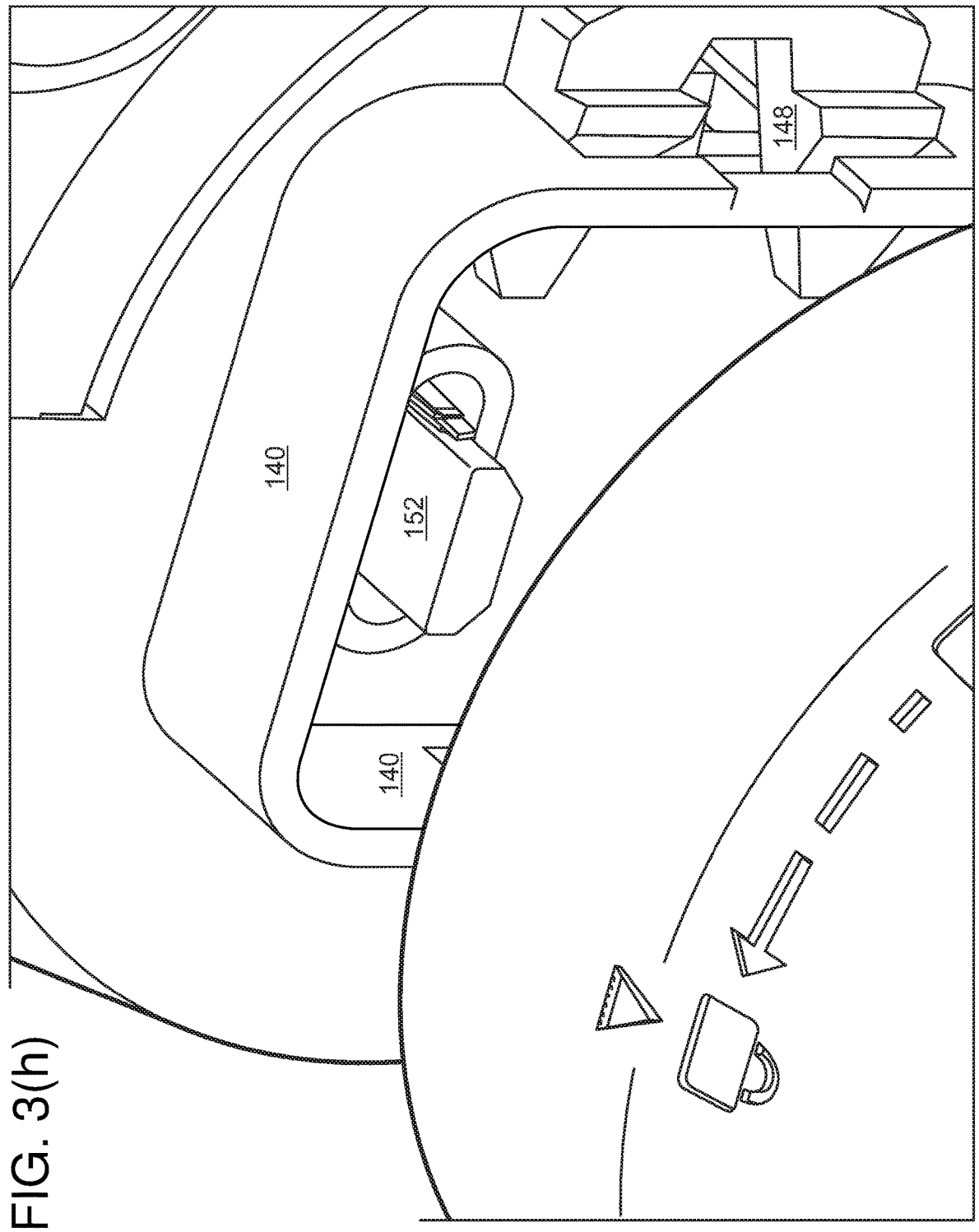
Figure 4A:
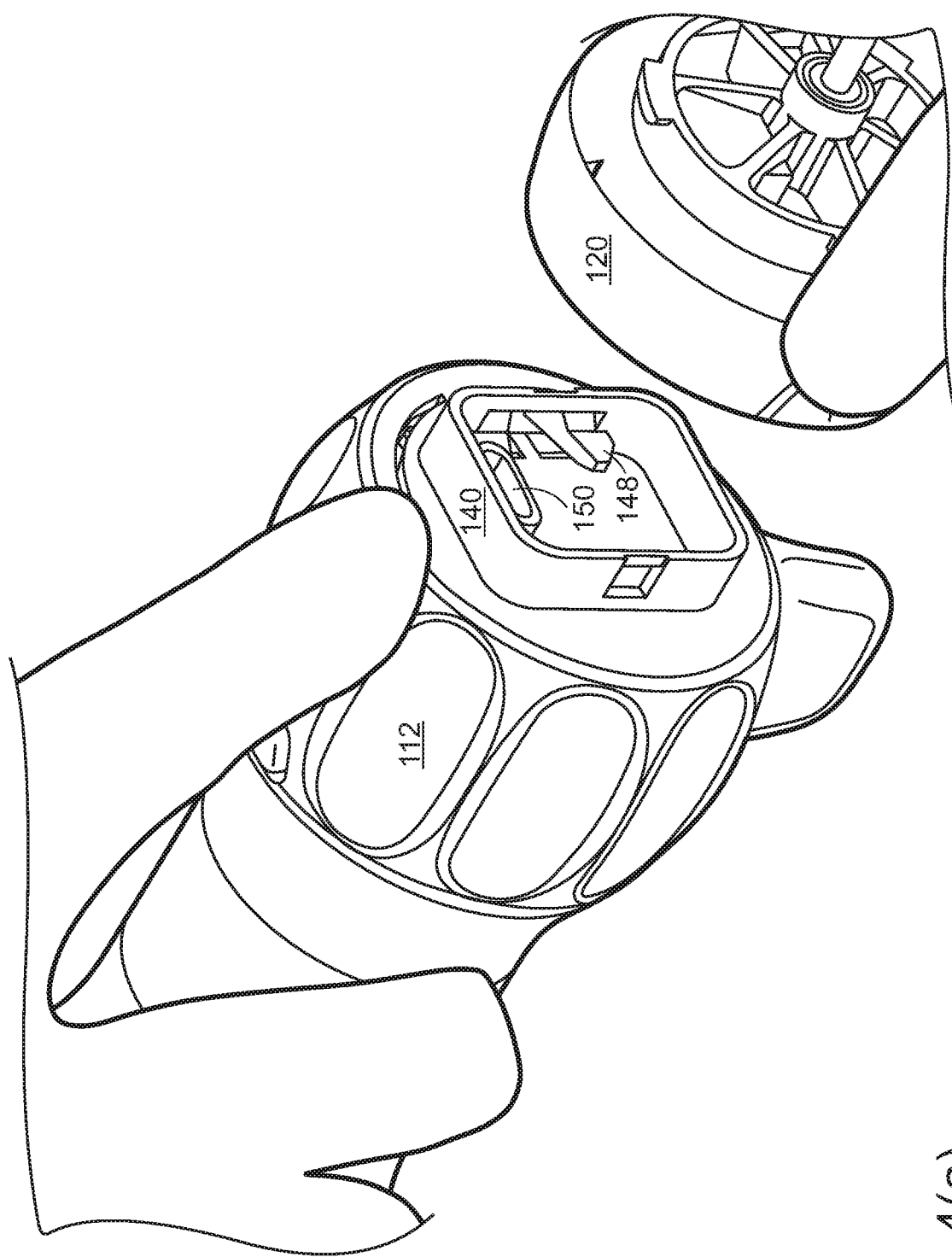
Figure 4B:
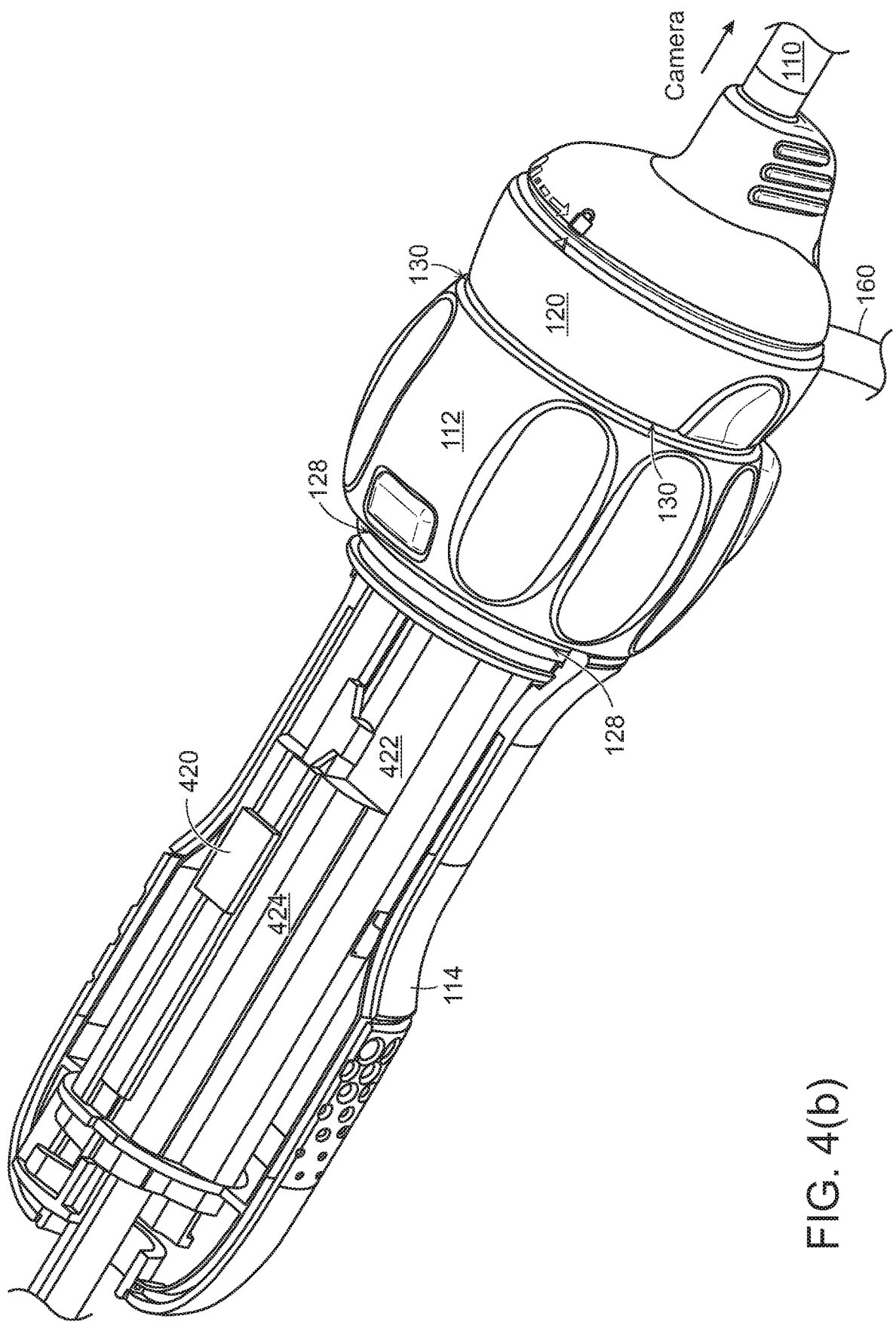
Figure 4C:
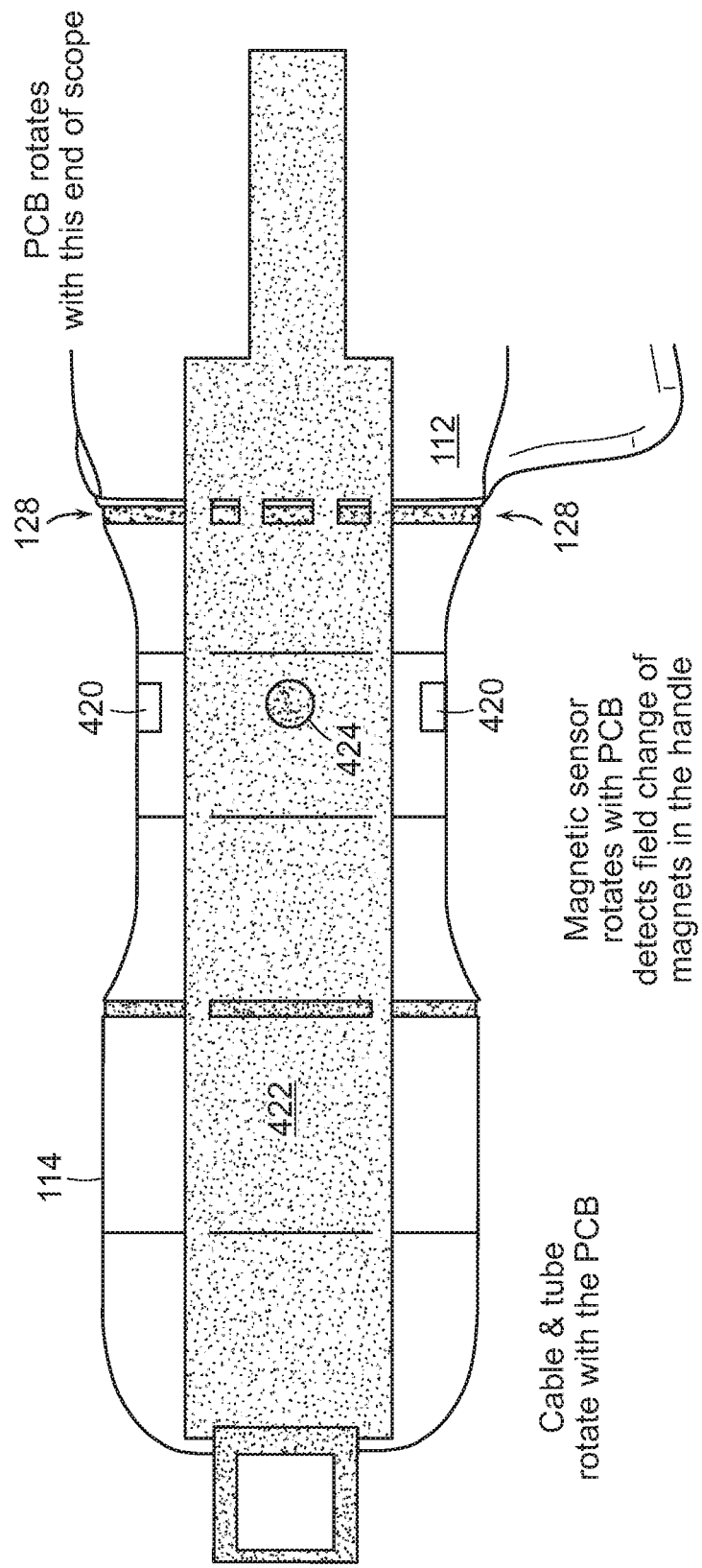
Figure 4D:
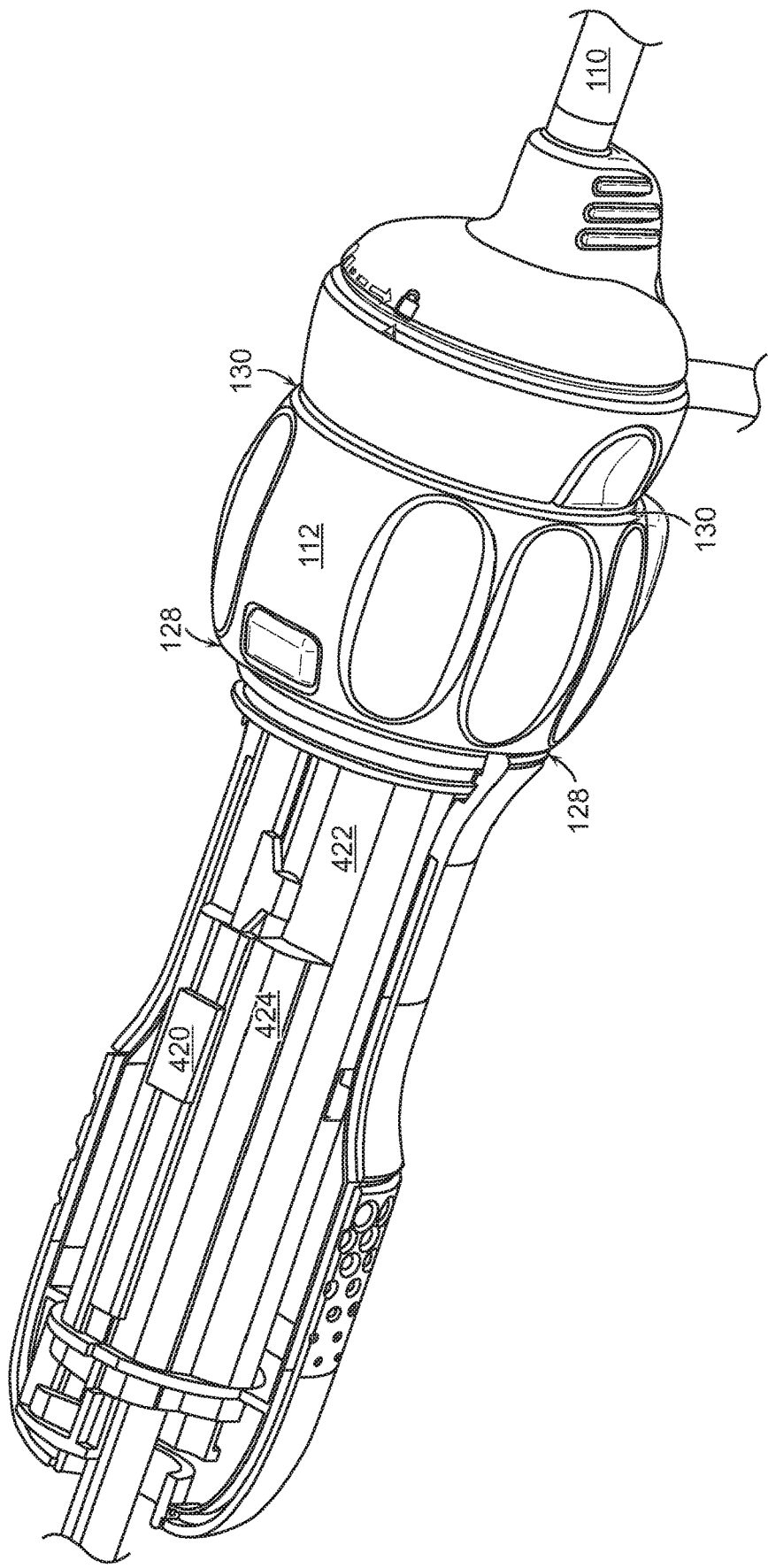

Referring to FIG. 1(b), disposable shaft portion 110, 120 may in turn be separable into an outer cannula 132 for protection and strength, and an inner shaft portion 134 carrying various illumination, optical, and fluid-carrying componentry.

III. Surgical Imaging Combining Visible and Nonvisible Light

A surgical endoscope may be equipped with image sensors 720 that image in nonvisible light, such as infrared or ultraviolet. Image processing techniques, especially those based on artificial intelligence and machine learning, may be used to enhance the nonvisible light image. Images formed from both visible and nonvisible signals may be displayed, either in split screen or as an integrated false color image, to a surgeon during surgery.

Illumination may be in visible light, infrared, and/or ultraviolet. In some cases, the illumination LED (light emitting diode) 730 may be placed in reusable handle 112, 114, and the disposable shaft 110 may have fiber optics to transmit light to the tip 116, and joint 130 may have an optical coupler. In other cases, the illumination LED 730 may be placed in tip 116 to illuminate the surgical cavity directly; in such cases, joint 130 may have a power connector. In some cases, the LED 730 may be recessed from the tip 116, or placed somewhere in the shaft 110, and optical fiber may early illumination light to the tip 116. The optical fiber may be configured, for example; with a split, so that light will be arrayed in a desired pattern around the image sensor 720 to better distribute the light into the surgical cavity around the image sensor 720.

Nonvisible light imaging may be useful in a variety of situations. Some nonvisible wavelengths transmit through tissue more easily than visible light does. In such cases, imaging from nonvisible spectrum may be combined with visible light imaging to reveal subsurface structure or physiology. In other cases, various tissues 760 reflect or fluoresce at varying wavelengths depending on physiological state. For example, tissues absorb light in the 320-380 nm (ultraviolet) range, and fluoresce at 440-480 nm (blue) more strongly when anoxic (oxygen starved) than when normoxic. In other cases, contrast dye 762 may be introduced into tissue 760 to fluoresce at certain wavelengths, to define tissue boundaries, or that fluoresces depending on physiological state. An endoscope that images in nonvisible wavelengths may provide 740 a surgeon with better information about tissues at a surgical site, allowing better surgical outcomes. In some cases, a single endoscope tip may sense at multiple wavelengths. In other cases, endoscopes with different imaging wavelength bands may be provided, to be used in alternation.

III.A. Imaging Sensors for Nonvisible Light

An endoscope may be equipped with imaging sensors 720 that image in nonvisible light, or sensors 720 that image in both visible light and nonvisible light. This may be accomplished by means such as—

A conventional CCD or CMOS sensor 720 array may be sensitive into the near infrared. For example, the red sensels (sensing image elements, the sensing equivalent of display pixels) may detect beyond the visible spectrum into the near infrared. This near infrared signal may be separated out, for example, by subtracting an image taken with another image sensor 720 with a narrower wavelength sensitivity band. The nonvisible image may be processed for display 740.

A CCD or CMOS image plane whose sensels are sensitive in four colors, for example, in infrared, red, green, and blue (as opposed to conventional visible light sensors 720 that image red, green, and blue) may be used.

Two image planes may be placed side-by-side, one a conventional RGB visible light image plane and one sensitive to nonvisible light. In such a case, the image-merging software may account for parallax effects of the spatial offset in addition to merging of images. This, in turn, may have the additional advantage of using the binocular parallax to resolve three-dimensional information.

The image plane may have a frequency-fitter shutter 722 that can be controlled to rapidly switch between visible-light bandpass to infrared bandpass, much as liquid crystal display planes switch between transparent and opaque, In general, it may be desirable to capture image data at a high frame rate. This may permit image processing software to employ sub-pixel analysis to recover higher resolution image data.

III.B. Illumination and Contrast for Nonvisible Imaging

An endoscope may be equipped with multiple illumination LEDs 730, one or more in visible wavelengths, and one or more in nonvisible wavelengths. The endoscope's field of view may be illuminated by tunable lasers, variable spectrum LEDs 730, pulse-width modulation among LEDs 730 of different wavelength, and similar techniques, to produce illumination of imaged tissue 760 in nonvisible wavelengths.

If the sensing CCD or CMOS planes 720 are undersensitive to some wavelengths, the illumination sources may be tuned to compensate by over-illuminating at those wavelengths.

Because LEDs 730 can be flashed extremely rapidly, multiple LEDs 730 of varying wavelength may be strobed 732 rapidly, frame-by-frame, to image at different wavelengths. Images at successive frames may be combined as discussed in section III.C, following.

In some cases, the tissue 760 may be dyed with a contrast 762, such as indocyanine green (ICG) which is used to visualize lymph nodes, lymphatic pathways, vessels, and tissue borders. For example, ICG may be used to identify lymph nodes in cancer surgery, or to identify diseased vs. healthy liver segments for liver resection. ICC fluoresces in near infrared. An endoscope that can image this infrared fluorescence may be used to more precisely identify tissue to be resected.

III.C. Image Processing

Image processing techniques 712 may be used to process the image, for example, to improve contrast, to extract features in under-saturated or oversaturated parts of the image, to sharpen edges, to identify structures and boundaries, etc. Image-matching or image-stitching technology 712 may be used to integrate multiple images from visible light and nonvisible light sensors 720 into a composed false color image. The image processing 712 may be based on artificial intelligence and machine learning techniques.

The images from the multiple image sensors 720 may be merged. Example image merging technologies include HDR (high dynamic range imaging) that receives multiple images of the same scene, taken in different lighting conditions, and uses the multiple images to correct for over-saturation and under-saturation in parts of the image. HDR techniques that learn via machine learning may be adapted for use with the multiple wavelengths imaged by an endoscope. Surgical video may be captured at high frame rates, and various video channels may be merged into lower frame-rate but higher image quality video. Known techniques for image merging of the various images may be used.

Feature recognition may be used to register the two images. Images from two different image sensors 720 may be brought into registration using stereoscopic vision registration techniques. If two image sensors 720 are spaced apart, parallax differences between the two image sensors 720 may be used to recover three-dimensional information.

Techniques for merging of single images may be used on successive frames of video to merge various video channels at different wavelengths.

A combined image may be formed by a number of false color rendering techniques. The nonvisible image may be preprocessed, for example to identify edges and to expand contrast. The visible image may be "squeezed" into part of the visible spectrum, so that the nonvisible image may be rendered in the freed-up part. The nonvisible image may be overlaid on the visible image using a part of the spectrum that does not otherwise appear in the image. The display system 740 may permit flashing back and forth between the visible image and an image rendered from the nonvisible sensors 720.

Multiple images taken in parallel in different lighting may be juxtaposed on a single split-screen display 740.

IV. Additional Features of an Endoscope

Referring to FIGS. 2(*a*), 2(*b*), 2(*c*), and 2(*d*), the endoscope may have a handle 112, 114, 120, and a shaft 110 for insertion into a body. At or near distal tip 116 of the shaft 110 may be a camera, electronic image sensor, or other optical component. The camera's orientation may be fixed in the scope, or may be pannable. The camera may be at tip 116, looking out from the shaft, or may be recessed a short distance behind the structural tip of the shaft. Also at or near the tip may be an illumination source, such as an LED. Tip 116 may have a rigid pointed tocar tip, or may have a spoon-shaped portion that reaches past the image sensor, or may be flexible (in the manner of the tip of a colonoscope), in each case extending a little beyond imaging camera to provide physical protection to the camera/image sensor during insertion or to protect the camera/image sensor from a surgical cutting device.

The shaft 110 itself may be rigid, made of a nonbioreactive metal such as stainless steel or coated aluminum. In some cases, a surgical cavity around the endoscope tip may be insufflated by gas (typically carbon dioxide), or irrigated by saline solution. In either case, fluid inflow and outflow may be effected by channels through the shaft.

Shaft 110 may also carry power wires to the illumination LED and the camera, and carry signal wires that carry an optical signal back from the camera to electronics in the reusable portion 112, 114 of the handle. Electrical power to the camera may be supplied over conductors in a flexible cable or on a printed circuit board (flexible or rigid), and insulated with a conformal and insulating coating such as parylene. This same flexible circuit board may have signal conductors for the video signal from the camera. The video signal may be transmitted from the camera to the handle using any video signal protocol, for example, MIPI (Mobile Industry Processor Interface) or HDMI. Parylene may also improve biocompatibility.

Shaft 110 may also carry cables or other mechanical elements to control panning of the camera.

Referring to FIG. 3(*a*), rotation collar may have various features that make rotation easy. For example, depressions 302 may provide a good grip for fingers for light roll torque. Fin 304 may provide greater leverage for greater roll torque, and may also provide a fixed rotational point of reference.

A button 310 may perform various functions, such as turning illumination LED on or off, taking pictures, starting and stopping video, and the like. A single button may perform all these functions based on the nature of the press. For example, press-and-hold for 3 seconds may turn the illumination LED on and off. A quick press may capture a single-frame still picture. A double-click may start and stop video recording.

If the camera at the tip 116 of shaft 110 is pannable or has other controllable features, there may be a control (for example, a lever, or a touch-slide panel, etc.) near button 310 to control that adjustment of the camera.

Referring to FIG. 3(*b*), the camera may be placed slightly remote from tip 116. Metal distal from the camera may be useful to protect the camera and its mounting from large forces that can exist during insertion into the surgery site, and may protect the camera from surgical instruments such as shavers and cutters, and keep the camera clean from bodily fluids. The space around the camera may be used to circulate insufflation fluid (water or gas) or cleaning fluid (typically water).

One or more ultraviolet LEDs may be placed inside handle 112,114, inside shaft 110, or near tip 116 to assist with insuring sterility of the internal components of the device or of the water as it passes thru the device Referring to FIG. 3(*c*), irrigation/insufflation hose(s) 160, 162 may enter at various points through the handle. For example, irrigation/insufflation hose(s) 160, 162 may enter through fin 304. Or, as shown in FIGS. 5(*a*), and 5(*b*), irrigation/insufflation fluid/gas hose(s) 160, 162 may enter through the proximal end of handle 114. This hose may then be disconnectable via a fluid disconnect joint 320 within joint 130. Referring to FIG. 3(*d*), in cases where hose(s) 160 for insufflation fluid/gas enters through disposable cap 120, various joints and strain relief features 340 may be used to hold hose(s) 160 in place.

Referring to FIG. 3(*e*) and FIG. 3(*h*), electrical connectors 150, 152 such as USB-C or mini-HDMI connectors may be used to connect the camera to a circuit board interior to handle 114.

Referring to FIG. 3(*e*), in cases where a hose 160 for insufflation fluid enters through reposable cap 120, various joints and strain relief features 340 may be used to hold hose 160 in place.

Referring to FIG. 3(*f*), rotation-locking coupling 140, 142 may lock disposable cap 120 in rotational relationship to rotation collar 112. Various rigid and resilient features 144, 148 may lock them together for other forces and torques, and release buttons 146 may permit them to disengage to allow replacement of disposable cap 120.

Referring to FIG. 3(*g*), rotation between the handle's stationary portion 114 and rotation collar 112 may be provided via a rotational bearing 360 at joint 128.

Referring to FIGS. 4(*b*) and 4(*c*), proximal handle 114 may contain a number of components, typically components that have only incidental patient contact (and therefore present less risk of cross-infection), are higher in cost (and therefore desirably reusable), and either sterilizeable or may be covered by a sterility sleeve. For example, proximal handle 114 may hold power transformers, signal amplifiers, controls for the illumination LED and camera, a mechanical control for panning the camera, rotation sensors for righting of an image from the camera, and the like. The handle may also include connections to external sources and destinations of power, signal, fluid, and the like.

Proximal handle 114 may include rotational sensors so that an angular orientation of the camera may be ascertained. For example, the inner surface of proximal handle 114 may mount one or more magnets 420, and printed circuit board 422 (which rotates with rotation collar 112 and disposable cap 120) may have sensors 424 that detect the magnets. This may be used to compute a rotational orientation, which may in turn be used to "right" the image from the camera on a video display screen.

The distal tip of the shaft, the camera mounted therein, and the mounting of componentry within the shaft may be designed to be robust. Occasionally, during surgery, the tip of the endoscope may come into contact with a shaver, ablation probe, or cauterization probe, and it may be desirable to have the tip be robust to such contacts. To reduce risk that componentry may be dislodged and left in the patient, the disposable shaft and its componentry may be designed to avoid joints that are at high risk of mechanical failure. A disposable optical system may prevent the image degradation that occurs when nondisposable optics are reused in multiple surgical procedures.

Endoscopes as a genus include arthroscopes, laparoscopes, colonoscopes, and other specialized scopes for various body cavities. For an arthroscope for joint surgery, the shaft may be as small as 5 mm, 5.5 mm, or 6 mm, and highly rigid. For other endoscopes, such as a colonoscope, the diameter may be larger, and the shaft may be flexible.

The endoscope may be delivered as a handle and multiple tips, each tip individually sealed for sterility.

Figure 6:
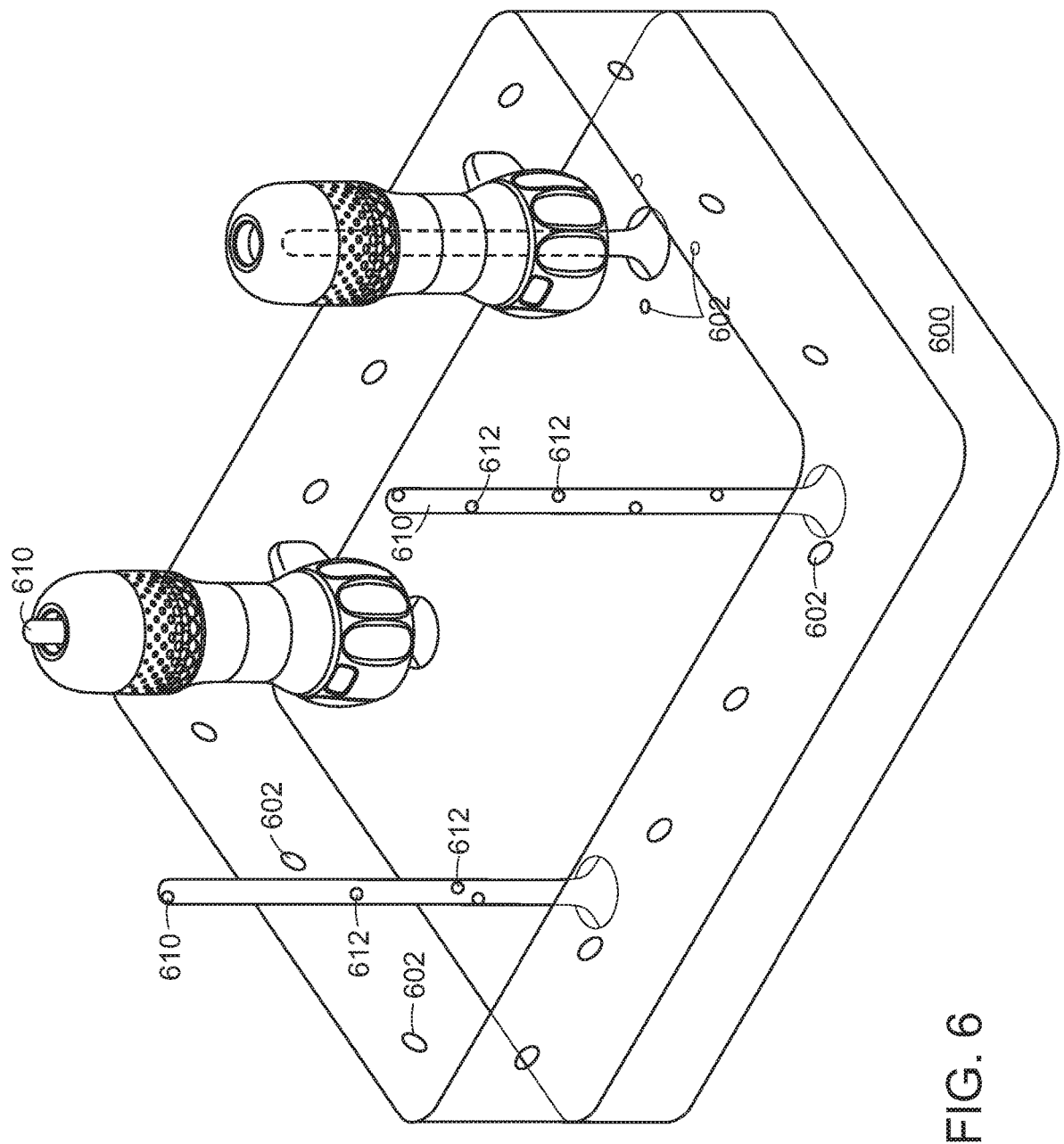
FIG. 6 is a perspective view of endoscope handles in a sterilizer.
Figure 7:
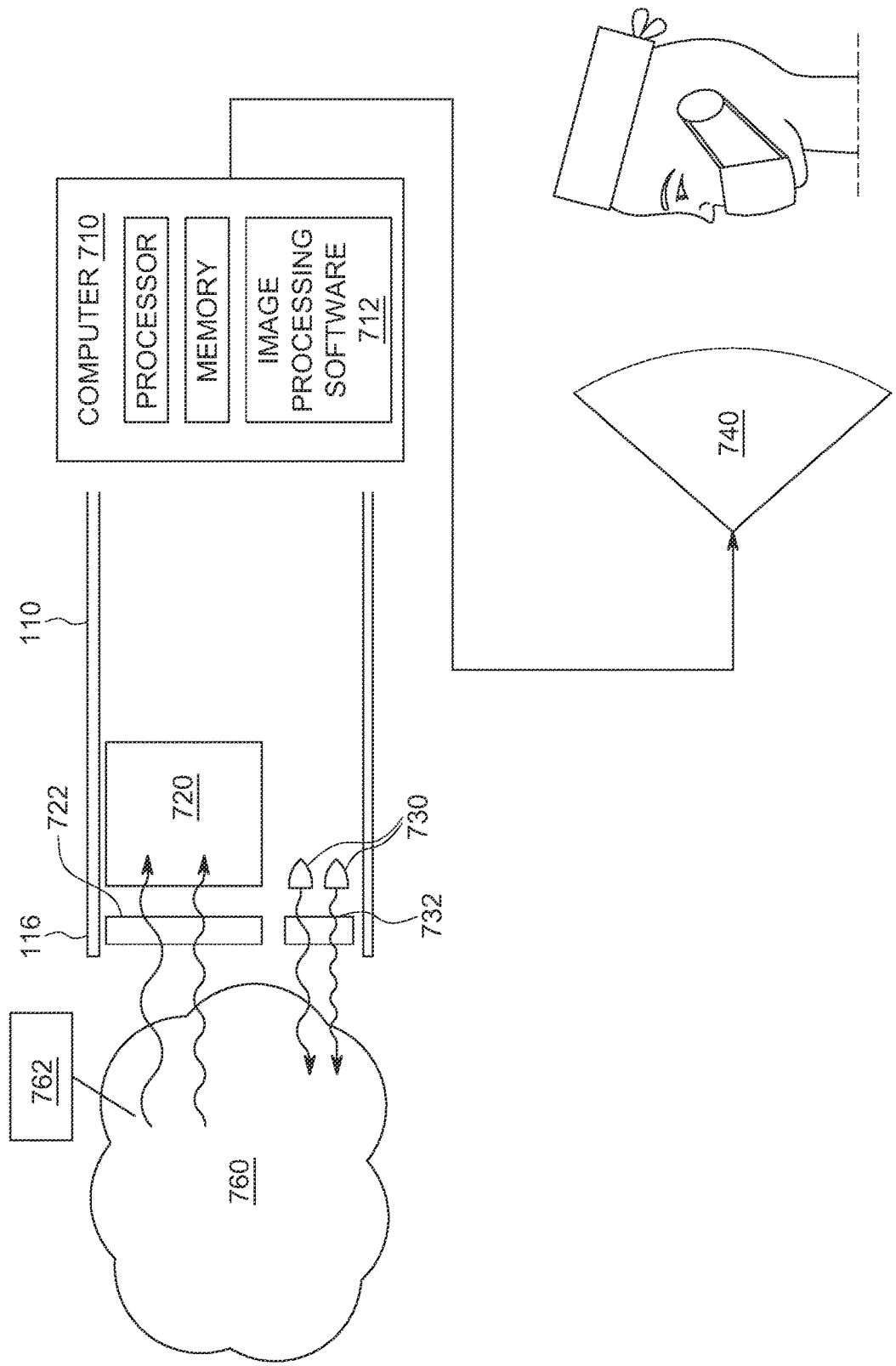
FIG. 7 shows an endoscope, cut away, with surrounding context.

Referring to FIG. 6, reusable handles 112, 114 may be sterilized in a sterilizer 600. Preferably, hose(s) 160, 162 and all other portions of endoscope 100 that come into contact with the patient, or with fluids that have come into contact with the patient, are disposable, and the design for reusable portions 112, 114 ensures that contamination is minimized through avoiding contact with the patient's bodily fluids. Sterilizer 600 may be arranged to accept one or more reusable handles 112, 114, and irradiate them with ultraviolet light from ultraviolet LEDs 602. Rods 610 that pass through handle channel 544 may have ultraviolet LEDs 612 arranged along their lengths, to sterilize internal channels 544.

V. Other Embodiments

In general, in a first aspect, the invention features an endoscope. The endoscope has a handle and an insertion shaft. The insertion shaft has solid state illumination and imaging circuitry at or near a tip designed to provide illumination and imaging of the interior of a body cavity for a surgeon during surgery. The proximal portion of the handle has electronics for drive of the illumination circuitry and to receive imaging signal from the imaging circuitry, the proximal handle portion being designed to permit sterilization between uses. A joint between the proximal handle portion and the insertion shaft is designed to separably connect the insertion shaft to the proximal handle portion. When it is separated, the joint permits removal of the insertion shaft for disposal and replacement. The joint is designed so that, when connected, the joint can transfer mechanical force from a surgeon's hand to the insertion shaft, and provides electrical connectivity between the proximal handle circuitry and the illumination and imaging circuitry.

In general, in a second aspect, the invention features a method for performance with an endoscope having a handle and an insertion shaft, the insertion shaft having solid state illumination and imaging circuitry at or near a tip designed to provide illumination and imaging of the interior of a body cavity for a surgeon during surgery, and the proximal portion of the handle having electronics for drive of the illumination circuitry and to receive imaging signal from the imaging circuitry, the proximal handle portion being designed to permit sterilization between uses; and a joint between the proximal handle portion and the insertion shaft designed to separably connect the insertion shaft to the proximal handle portion. The joint is separated to permit removal of the insertion shaft for disposal and replacement. The joint is reconnected with a new insertion shaft, the connection designed to provide mechanical force transfer between a surgeon's hand to the insertion shaft, and electrical connectivity between the proximal handle circuitry and the illumination and imaging circuitry.

Embodiments of the invention may include one or more of the following features. The handle may have proximal and distal portions. The distal portion may lie between the insertion shaft and proximal handle portion. The insertion shaft may be rigidly affixed to the distal handle portion. The joint may be disposed to connect and disconnect the distal and proximal portions of the handle. The distal handle portion may be designed to indirectly transfer mechanical force between a surgeon's hand to the insertion shaft, and provide indirect electrical connectivity between the proximal handle circuitry and the illumination and imaging circuitry. The handle may have a rotation collar having surface features designed to assist the surgeon in rotating the insertion shaft in the roll dimension about the axis of the insertion shaft relative to the proximal handle portion. The electronics inside the proximal handle portion may be designed to sense roll of the insertion shaft, and provide an angular rotation signal designed to permit righting of a displayed image received from the imaging circuitry. A mounting for the image sensor may be designed to permit panning of the image sensor about a pitch or yaw axis perpendicular to the central axis of the insertion shaft. One or more ultraviolet LEDs internal to the endoscope may be designed to sterilize a region of the interior of the endoscope. Hoses for insufflation fluid or gas may be designed on lie on or near a central axis of proximal handle portion. Two or more insertion shafts each having dimensions different than the others, may each be connectable to the proximal handle portion at the joint, to permit use of the proximal handle in surgery with different requirements for insertion shaft. A sterilization cabinet may be designed to sterilize components of the endoscope.

Various processes described herein may be implemented by appropriately programmed general purpose computers, special purpose computers, and computing devices. Typically a processor (e.g., one or more microprocessors, one or more microcontrollers, one or more digital signal processors) will receive instructions (e.g., from a memory or like device), and execute those instructions, thereby performing one or more processes defined by those instructions. Instructions may be embodied in one or more computer programs, one or more scripts, or in other forms. The processing may be performed on one or more microprocessors, central processing units (CPUs), computing devices, microcontrollers, digital signal processors, or like devices or any combination thereof. Programs that implement the processing, and the data operated on, may be stored and transmitted using a variety of media. In some cases, hard-wired circuitry or custom hardware may be used in place of, or in combination with, some or all of the software instructions that can implement the processes. Algorithms other than those described may be used.

Programs and data may be stored in various media appropriate to the purpose, or a combination of heterogenous media that may be read and/or written by a computer, a processor or a like device. The media may include non-volatile media, volatile media, optical or magnetic media, dynamic random access memory (DRAM), static ram, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge or other memory technologies. Transmission media include coaxial cables, copper wire and fiber optics, including the wires that comprise a system bus coupled to the processor.

Databases may be implemented using database management systems or ad hoc memory organization schemes. Alternative database structures to those described may be readily employed. Databases may be stored locally or remotely from a device which accesses data in such a database.

In some cases, the processing may be performed in a network environment including a computer that is in communication (e.g., via a communications network) with one or more devices. The computer may communicate with the devices directly or indirectly, via any wired or wireless medium (e.g. the Internet, LAN, WAN or Ethernet, Token Ring, a telephone line, a cable line, a radio channel, an optical communications line, commercial on-line service providers, bulletin board systems, a satellite communications link, a combination of any of the above). Transmission media may include coaxial cables, copper wire and fiber optics, including the wires that comprise a system bus coupled to the processor. Transmission may occur over transmission media, or over electromagnetic waves, such as via infrared, WiFi, Bluetooth, and the like, at various frequencies using various protocols. Each of the devices may themselves comprise computers or other computing devices, such as those based on the Intel® Pentium® or Centrino™ processor, that are adapted to communicate with the computer. Any number and type of devices may be in communication with the computer.

A server computer or centralized authority may or may not be necessary or desirable. In various cases, the network may or may not include a central authority device. Various processing functions may be performed on a central authority server, one of several distributed servers, or other distributed devices.

For the convenience of the reader, the above description has focused on a representative sample of all possible embodiments, a sample that teaches the principles of the invention and conveys the best mode contemplated for carrying it out. The invention is not limited to the described embodiments. Well known features may not have been described in detail to avoid unnecessarily obscuring the principles relevant to the claimed invention. Throughout this application and its associated file history, when the term "invention" is used, it refers to the entire collection of ideas and principles described; in contrast, the formal definition of the exclusive protected property right is set forth in the claims, which exclusively control. The description has not attempted to exhaustively enumerate all possible variations. Other undescribed variations or modifications may be possible. Where multiple alternative embodiments are described, in many cases it will be possible to combine elements of different embodiments, or to combine elements of the embodiments described here with other modifications or variations that are not expressly described. A list of items does not imply that any or all of the items are mutually exclusive, nor that any or all of the items are comprehensive of any category, unless expressly specified otherwise. In many cases, one feature or group of features may be used separately from the entire apparatus or methods described. Many of those undescribed alternatives, variations, modifications and equivalents are within the literal scope of the following claims, and others are equivalent. The claims may be practiced without some or all of the specific details described in the specification. In many cases, method steps described in this specification can be performed in different orders than that presented in this specification, or in parallel rather than sequentially, or in different computers of a computer network, rather than all on a single computer.

The invention claimed is:

1. An endoscope, comprising:
  one or more image sensors designed to capture image data in visible light and image data in a nonvisible portion of the electromagnetic spectrum, sensels of the one or more image sensors having overlapping wavelength sensitivity bands;
  an insertion shaft designed to support the one or more image sensors at or near a distal tip, the insertion shaft and support designed to support the one or more image sensors for endoscopic insertion to a surgical site in a human body;
  a plurality of light emitting diodes (LEDs) of different wavelengths, designed to deliver illumination to the surgical site, including at least one LED to emit in visible wavelengths and at least one wavelength to emit at one or more wavelengths designed to induce fluorescence;

illumination intensity of the LEDs and sensor sensitivity of the image sensors being designed to compensate for each other; and image processing software trained through machine learning to enhance image quality of at least the nonvisible portion of the image, including by subtraction of values of one sensel from another with an overlapping wavelength sensitivity band to recover an image value in the wavelength range of the non-overlap, and to present the enhanced nonvisible image as a real-time, visible presentation to a surgeon.

2. The endoscope of claim 1, wherein:
the software is programmed to display the visible presentation of the nonvisible image as a split-screen display with the visible light image data.

3. The endoscope of claim 1, wherein:
the software is programmed to display the visible presentation of the nonvisible image overlaid or merged with the visible light image data.

4. The endoscope of claim 3, wherein:
the software is programmed to overlay or merge the nonvisible image with the visible light image data by registering for parallax differences.

5. The endoscope of claim 3, wherein:
the software is programmed to overlay or merge the nonvisible image with the visible light image data by recovering three-dimensional spatial relationships.

6. The endoscope of claim 1, further comprising:
an ultraviolet LED mounted within the endoscope to illuminate tissue in the field of view of the nonvisible image sensor.

7. The endoscope of claim 1, further comprising:
an infrared LED mounted within the endoscope to illuminate tissue in the field of view of the nonvisible image sensor.

8. The endoscope of claim 1, wherein:
the one or more image sensors designed to capture image data in visible light and the one or more image sensors designed to capture image data in a nonvisible portion of the electromagnetic spectrum are designed into a single image plane.

9. The endoscope of claim 1, wherein:
an electronic shutter designed to chop for alternate illumination between multiple illumination sources of differing wavelength or alternate sensing between image sensors of differing wavelength sensitivity.

10. The endoscope of claim 1, wherein:
a strobe circuit designed to chop for alternate illumination between multiple illumination sources of differing wavelength.

11. The endoscope of claim 1, wherein:
the one or more image sensors designed to capture image data in visible light, the one or more image sensors designed to capture image data in a nonvisible portion of the electromagnetic spectrum, and image processing software are designed to capture image data from tissue below a surface at the field of view of the image sensors.

12. A method, comprising the steps of:
at a computer image processor, receiving image data from:
one or more image sensors designed to capture image data in visible light and image data in a nonvisible portion of the electromagnetic spectrum, sensels of the one or more image sensors having overlapping wavelength sensitivity bands;

the one or more visible and nonvisible image sensors being supported on an insertion shaft at or near a distal tip, the insertion shaft and support designed to support the one or more image sensors for endoscopic insertion to a surgical site in a human body;

the surgical site to be illuminated by a plurality of light emitting diodes (LEDs) of different wavelengths, designed to deliver illumination to the surgical site, including at least one LED to emit in visible wavelengths and at least one wavelength to emit at one or more wavelengths the designed to induce fluorescence;

illumination intensity of the LEDs and sensor sensitivity of the image sensors being designed to compensate for each other; and processing the image information through machine learning image processing trained to enhance image quality of at least the nonvisible portion of the image, including by subtraction of values of one sensel from another with an overlapping wavelength sensitivity band to recover an image value in the wavelength range of the non-overlap; and presenting the enhanced nonvisible image as a real-time, visible presentation to a surgeon.

13. The method of claim 12, further comprising the step of:
processing the image data for display of the visible presentation of the nonvisible image overlaid or merged with the visible light image data.

14. The method of claim 13, further comprising the step of:
processing the image data to overlay or merge the nonvisible image with the visible light image data by registering for parallax differences.

15. The method of claim 14, further comprising the step of:
processing the image data to overlay or merge the nonvisible image with the visible light image data by recovering three-dimensional spatial relationships.

16. The method of claim 12, further comprising the step of:
the one or more image sensors designed to capture image data in visible light and the one or more image sensors designed to capture image data in a nonvisible portion of the electromagnetic spectrum are designed into a single image plane.

17. The method of claim 12, further comprising the step of:
flashing an electronic shutter designed to chop for alternate illumination between multiple illumination sources of differing wavelength or alternate sensing between image sensors of differing wavelength sensitivity.

18. The method of claim 12, further comprising the step:
strobing for alternate illumination between multiple illumination sources of differing wavelength.

19. The method of claim 12, wherein:
the one or more image sensors designed to capture image data in visible light and the one or more image sensors designed to capture image data in a nonvisible portion of the electromagnetic spectrum and image processing software are designed to capture image data from tissue below a surface at the field of view of the image sensors.

20. The method of claim 12, further comprising the step of:
    infusing tissue in the field of view of the nonvisible image sensor with contrast fluorescent dye.

* * * * *